US006977244B2

(12) United States Patent
Tormo et al.

(10) Patent No.: US 6,977,244 B2
(45) Date of Patent: Dec. 20, 2005

(54) INHIBITION OF BCL-2 PROTEIN EXPRESSION BY LIPOSOMAL ANTISENSE OLIGODEOXYNUCLEOTIDES

(75) Inventors: Mar Tormo, Valencia (ES); Ana M. Tari, Houston, TX (US); Gabriel Lopez-Berestein, Bellaire, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 08/726,211

(22) Filed: Oct. 4, 1996

(65) Prior Publication Data

US 2003/0012812 A1 Jan. 16, 2003

(51) Int. Cl.[7] .................. A61K 48/00; C07H 21/04; C12N 15/88
(52) U.S. Cl. .................. 514/44; 435/375; 435/458; 424/450; 536/24.5
(58) Field of Search .................. 424/450; 435/375, 435/458; 514/44; 536/24.5

(56) References Cited

U.S. PATENT DOCUMENTS

| | | | |
|---|---|---|---|
| 4,229,360 A | 10/1980 | Schneider et al. | 260/403 |
| 4,394,448 A | 7/1983 | Szoka, Jr. et al. | 435/172 |
| 4,469,863 A | 9/1984 | Ts'o et al. | 536/27 |
| 4,480,041 A | 10/1984 | Myles et al. | 436/508 |
| 4,721,612 A | 1/1988 | Janoff et al. | 424/1.21 |
| 4,835,263 A | 5/1989 | Nguyen et al. | 536/27 |
| 4,837,028 A | 6/1989 | Allen | 424/450 |
| 4,904,582 A | 2/1990 | Tullis | 435/6 |
| 4,920,016 A | 4/1990 | Allen et al. | 424/450 |
| 4,924,624 A | 5/1990 | Suhadolnik et al. | 514/44 |
| 4,950,432 A | 8/1990 | Mehta et al. | 264/4.6 |
| 5,015,568 A | 5/1991 | Tsujimoto et al. | 435/5 |
| 5,030,442 A | 7/1991 | Uster et al. | 424/45 |
| 5,049,388 A | 9/1991 | Knight et al. | 424/450 |
| 5,087,617 A | 2/1992 | Smith | 514/44 |
| 5,094,785 A | 3/1992 | Law et al. | 264/4.3 |
| 5,098,890 A | 3/1992 | Gewirtz et al. | 514/44 |
| 5,100,662 A | 3/1992 | Bolcsak et al. | 424/450 |
| 5,112,962 A | 5/1992 | Letsinger et al. | 536/25.3 |
| 5,135,917 A | 8/1992 | Burch | 514/44 |
| 5,178,875 A | 1/1993 | Lenk et al. | 424/450 |
| 5,188,897 A | 2/1993 | Suhadolnik et al. | 428/402.2 |
| 5,202,429 A | 4/1993 | Tsujimoto et al. | 536/23.5 |
| 5,227,170 A | 7/1993 | Sullivan | 424/450 |
| 5,248,671 A | 9/1993 | Smith | 514/44 |
| 5,264,618 A | 11/1993 | Felgner et al. | 560/224 |
| 5,271,941 A | 12/1993 | Cho-Chung | 424/450 |
| 5,279,833 A | 1/1994 | Rose | 424/450 |
| 5,279,957 A | 1/1994 | Gross | 435/348 |
| 5,320,962 A | 6/1994 | Stiles et al. | 435/252.3 |
| 5,324,654 A | 6/1994 | Bredesen | 435/376 |
| 5,376,646 A | 12/1994 | Pittrof et al. | 514/78 |
| 5,378,825 A | 1/1995 | Cook et al. | 536/25.34 |
| 5,417,978 A * | 5/1995 | Tari et al. | 424/450 |
| 5,459,251 A | 10/1995 | Tsujimoto et al. | 536/23.5 |
| 5,527,538 A | 6/1996 | Baldeschwieler | 424/1.21 |
| 5,539,085 A | 7/1996 | Bischoff et al. | 530/350 |
| 5,539,094 A | 7/1996 | Reed et al. | 536/23.5 |
| 5,560,923 A | 10/1996 | Rahman et al. | 424/450 |
| 5,565,337 A | 10/1996 | Diamond et al. | 435/70.2 |
| 5,583,034 A * | 12/1996 | Green et al. | 435/240.2 |
| 5,622,852 A | 4/1997 | Korsmeyer | 435/325 |
| 5,641,662 A | 6/1997 | Debs et al. | 435/458 |
| 5,661,018 A | 8/1997 | Ashley et al. | 435/172.3 |
| 5,665,710 A | 9/1997 | Rahman et al. | 514/44 |
| 5,696,248 A | 12/1997 | Peyman et al. | 536/22.1 |
| 5,705,385 A | 1/1998 | Bally et al. | 435/320.1 |
| 5,734,033 A | 3/1998 | Reed | 536/23.1 |
| 5,750,669 A | 5/1998 | Rosch et al. | 536/24.3 |
| 5,756,122 A | 5/1998 | Thierry et al. | 424/450 |
| 5,817,811 A | 10/1998 | Breipohl et al. | 544/264 |
| 5,831,048 A | 11/1998 | Schweighoffer et al. | 536/23.1 |
| 5,831,066 A | 11/1998 | Reed | 536/24.5 |
| 5,837,838 A | 11/1998 | Reed et al. | 536/23.1 |
| 5,855,911 A | 1/1999 | Lopez-Berestein et al. | 424/450 |
| 5,874,224 A | 2/1999 | Bandman et al. | 435/6 |
| 5,874,553 A | 2/1999 | Peyman et al. | 536/22.1 |
| 5,891,714 A | 4/1999 | Ashley et al. | 435/320.1 |
| 5,908,635 A | 6/1999 | Thierry | 424/450 |
| 5,976,567 A | 11/1999 | Wheeler et al. | 454/450 |
| 5,981,501 A | 11/1999 | Wheeler et al. | 514/44 |
| 5,989,912 A | 11/1999 | Arrow et al. | 435/375 |
| 6,015,886 A | 1/2000 | Dale et al. | 536/23.1 |
| 6,030,954 A | 2/2000 | Wu et al. | 514/44 |
| 6,034,235 A | 3/2000 | Sugiyama et al. | 536/24.5 |
| 6,040,181 A | 3/2000 | Reed | 435/377 |
| 6,042,846 A | 3/2000 | Lopez-Berestein et al. | 424/450 |
| 6,096,720 A | 8/2000 | Love et al. | 514/44 |
| 6,110,490 A | 8/2000 | Thierry | 424/450 |
| 6,120,794 A | 9/2000 | Liu et al. | 424/450 |

(Continued)

FOREIGN PATENT DOCUMENTS

| | | |
|---|---|---|
| CA | 2171589 | 3/1996 |
| WO | WO 88/04924 | 7/1988 |
| WO | WO 89/06977 | 8/1989 |

(Continued)

OTHER PUBLICATIONS

Far et al. Concepts to automate the theoretical design of effective antisense oligonucleotides. Bioinformatics. Nov. 2001;17(11):1058–61.*

(Continued)

*Primary Examiner*—David Guzo
*Assistant Examiner*—Daniel M. Sullivan
(74) *Attorney, Agent, or Firm*—Fulbright & Jaworski L.L.P.

(57) ABSTRACT

The present invention provides novel compositions and methods for use in the treatment of Bcl-2-associated diseases like cancer, specifically, in the treatment of follicular lymphoma (FL). The compositions contain antisense oligonucleotides that hybridize to Bcl-2 nucleic acids, the gene products of which are known to interact with the tumorigenic protein Bcl-2. Used alone, or in conjunction with other antisense oligonucleotides, these compositions inhibit the proliferation of FL cancer cells.

43 Claims, 8 Drawing Sheets

U.S. PATENT DOCUMENTS

| | | | |
|---|---|---|---|
| 6,120,798 A | 9/2000 | Allen et al. | 424/450 |
| 6,126,965 A | 10/2000 | Kasid et al. | 424/450 |
| 6,136,965 A | 10/2000 | Bruice et al. | 536/25.3 |
| 6,211,162 B1 | 4/2001 | Dale et al. | 514/44 |
| 6,211,349 B1 | 4/2001 | Dale et al. | 536/23.1 |
| 6,277,832 B1 | 8/2001 | Sugiyama et al. | 514/44 |
| 6,277,981 B1 | 8/2001 | Tu et al. | 536/25.3 |
| 6,291,668 B1 | 9/2001 | Ziegler et al. | 536/24.5 |
| 6,326,487 B1 | 12/2001 | Peyman et al. | 536/24.5 |

FOREIGN PATENT DOCUMENTS

| | | |
|---|---|---|
| WO | WO 90/09180 | 8/1990 |
| WO | WO 90/10488 | 9/1990 |
| WO | WO 91/16901 | 11/1991 |
| WO | WO 92/21330 | 12/1992 |
| WO | WO 93/07883 | 4/1993 |
| WO | WO 93/11245 | 6/1993 |
| WO | WO 93/20200 * | 10/1993 |
| WO | WO 93/24653 | 12/1993 |
| WO | WO 94/04545 | 3/1994 |
| WO | WO 94/05259 | 3/1994 |
| WO | WO 95/03788 | 2/1995 |
| WO | WO 95/08350 * | 3/1995 |
| WO | WO 95/28497 | 10/1995 |
| WO | WO 96/27663 | 9/1996 |
| WO | WO 96/40062 | 12/1996 |
| WO | WO 97/07784 | 3/1997 |
| WO | WO 98/14172 | 4/1998 |
| WO | WO 98/56905 | 12/1998 |
| WO | WO 00/40595 | 7/2000 |
| WO | WO 02/17852 | 3/2002 |

OTHER PUBLICATIONS

Braasch et al. Novel antisense and peptide nucleic acid strategies for controlling gene expression. Biochemistry. Apr. 9, 2002;41(14):450–10.*

Tamm et al. Antisense therapy in oncology: new hope for an old idea? Lancet. Aug. 11, 2001;358(9280):489–97.*

Abubakr et al. (1994) Effectiveness of Bcl–2 antisense oliogodeoxynucleotides (AS–ODN) against human follicular small–cleaved cell lymphoma (FSCCL)–SCID mice xenograft model. Blood 84 (10 Suupl 1)374A, Dec. 1994.*

Pocock et al. (1993) In vivo suppression of B–cell lymphoma with Bcl–2 antisense oligonucleotides. Blood 82 (10 Suppl 1) 200A, Dec. 1993.*

Cotter et al. (1994) Antisense oligonucleotides suppress B–cell lymphoma growth in a SCID–hu mouse model. Oncogene 9:3049–3055, Oct. 1994.*

Ledley (1994) Non–viral gene therapy. Curr. Opin. Biotechnol. 5:626–636.*

Rojanasakul (1996) Antisense oligonucleotide therapeutics: drug delivery and targeting. Adv. Drug Delivery Rev. 18:115–131.*

Tormo et al. (1996) Antitumor activity of liposomal–bcl–2–antisense oligonucleotides in follicular lymphoma. Proc. Amer. Assoc. Cancer Res. 37:173, Mar. 1996.*

Almazan et al. (1996) Methylphosphonate–containing oligonucleotides efficiently and specifically inhibit bcl–2 and erbB–2 expression in vitro. Proc. Amer. Assoc. Cancer Res. 37:353, Mar. 1996.*

Agrawal, "Antisense oligonucleotides; towards clinical trials," TIB Tech, 14(10):376–387, 1996.

Agrawal et al., "Antisense therapeutics: is it as simple as complementary base recognition," Molecular Medicine Today, 6:72–81, 2000.

Aisenberg, "Coherent view of non–Hodgkin's lymphoma," J. Clin. Oncol., 13(10):2656–2675, 1995.

Baichwal and Sugden, "Vectors for gene transfer derived from animal DNA viruses: Transient and stable expression of transferred genes," In: Kucherlapati R, (ed.) Gene transfer. New York: Plenum Press, pp. 117–148, 1986.

Bangham et al., "Diffusion of univalent ions accross the lamellae of swollen phospholipids," J. Mol. Biol., 13:238–252, 1965.

Benvenisty and Reshif, "Direction introduction of genes into rats and expression of the genes," Proc. Nat'l Acad. Sci. USA, 83:9551–9555, 1986.

Chang et al., "Foreign gene delivery and expression in hepatocytes using a hepatitis B virus vector," Abstract, Hepatology, 14(4):124A, 1991.

Chen and Okayama, "High–efficiency transfection of mammalian cells by plasmid DNA," Mol. Cell Biol., 7(8):2745–2752, 1987.

Chirila et al., "The use of synthetic polymers for delivery of therapeutic antisense oligodeoxynucleotides," Biomaterials, 23:321–342, 2002.

Coffin, "Retroviridae: the viruses and their replication," In: Virology, Fields et al. (eds.), New York: Raven Press, pp. 1767–1847, 1996.

Cotter et al., "Human Bcl–2 antisense therapy for lymphomas," Biochimica et Biophysica Acta, 1489:97–106, 1999.

Coupar et al., "A general method for the construction of recombinant vaccinia virus expressing multiple foreign genes," Gene, 68:1–10, 1988.

Crooke, "Antisense research and application," Springer, NY, 1–50, 1998.

Crystal, Science, 270:404–410, 1995.

Deamer and Uster, "Liposome Preparation: Methods and Mechanisms," Liposomes, M. Ostro ed. (1983).

Dubensky et al., "Direct transfection of viral and plasmid DNA into the liver or spleen of mice," Proc. Nat'l Acad. Sci. USA, 81:7529–7533, 1984.

Fecheimer et al., "Transfection of mammalian cells with plasmid DNA by scrape loading and sonication loading," Proc. Nat'l Acad. Sci. USA, 84(23):8463–8467, 1987.

Fraley et al., "Entrapment of a bacterial plasmid in phospholipid vesicles: potential for gene transfer," Proc. Nat'l Acad. Sci. USA, 76(7):3348–3352, 1979.

Friedman et al., "CCAAT/enhancer–binding protein activates the promoter of the serum albumin gene in cultured hepatoma cells," Genes & Devel. 3:1314–1322, 1989.

Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87–103, 1991.

Gleave et al., "Targeting bcl–2 gene to delay androgen–independent progression and enhance chemosensitivity in prostate cancer using antisense bcl–2 oligodeoxynucleotides," Urology, 54(Suppl 6A):36–46, 1999.

Gopal, "Gene transfer method for transient gene expression, stable transformation, and cotransformation of suspension cell cultures," Mol. Cell Biol., 5:1188–1190, 1985.

Graham and van der Eb, "A new technique for the assay of infectivity of human adenovirus 5 DNA,", Virology, 52:456–467, 1973.

Graham et al., "Characteristics of a human cell line transformed by DNA from human adenovirus type 5," *J. Gen. Virol.*, 36:59–72, 1977.

Harland and Weintraub, "Translation of mammalian mRNA injected into *Xenopus oocytes* is specifically inhibited by antisense RNA," *J. Cell Biol.*, 101:1094–1099, 1985.

Hermonat and Muzycska, "Use of adeno–associated virus as a mammalian DNA cloning vector: Transduction of neomycin resistance into mammalian tissue culture cells," *Proc. Nat'l Acad. Sci. USA*, 81:6466–6470, 1984.

Horwich et al., "Synthesis of hepadnavirus particles that contain replication–defective duck hepatitis B virus genomes in cultured HuH7 cells," *J. Virol.* 64(2):642–650, 1990.

Jansen et al., "bcl–2 antisense therapy chemosensitizes human melanoma in SCID mice," *Nature Medicine*, 4(2):232–234, 1998.

James, "Towards gene–inhibition therapy: a review of progress and prospects in the field of antiviral antisense nucleic acids and ribozymes," Antiviral Chemistry and Chemotherapy, 2(4):191–215, 1991.

Johnson et al., "Patterns of survival in patients with recurrent follicular lymphoma: a 20–year study from a single center," *J. Clin. Oncol.*, 13(1):140–147, 1995.

Klein et al., "High–velocity microprojectiles for delivering nucleic acids into living cells," *Nature*, 327:70–73, 1987.

Konopleva et al., "Inhibition of Bcl–2 with liposomal P–ethoxy antisense oligonucleotides induces apoptosisin the presence of high level of Bcl–Xl and is critically depending on baseline Bcl–2 levels in AML," *J. Amer. Soc. Hamagology*, 92(10)Suppl. 1, Part 1 of 2, Abstract No. 2100, 1998.

Mann et al., "Construction of a retrovirus packaging mutant and its uses to produce helper–free defective retrovirus," *Cell*, 33:153–159, 1983.

McDonnell and Korsmeyer, "Progression from lymphoid hyperplasia to high–grade malignant lymphoma in mice transgenic for the t(14;18)," *Nature*, 349:254–256, 1991.

Milner et al., "Selecting effective antisense reagents on combinatorial oligonucleotide arrays," *Nature*, 15:537–541, 1997.

Miyake et al., "Antisense Bcl–2 oligodeoxynucleotides inhibit progression to androgen–independence after castration in the Shionogi tumor model," *Cancer Res.*, 59:4030–4034, 1999.

Neilan et al., "An African Swine fever virus with similarity to the protooncogene *blc–2* and the Epstein–Barr virus gene *BHRF1,*" *J. Virol.*, 67(7):4391–4394, 1993.

Nicolas and Rubenstein, "Retroviral vectors," *In: Vectors: A survey of molecular cloning vectors and their uses*, Rodriguez and Denhardt, (eds.), Stoneham: Butterworth, pp. 494–513, 1988.

Paskind et al., "Dependence of moloney murine leukemia virus production on cell growth," *Virology*, 67:242–248, 1975.

Palu et al., "In pursuit of new developments for gene therapy of human diseases," *Biotech.*, 68:1–13, 1999.

Pearson et al., "Identification of an Epstein–Barr virus early gene encoding a second component of the restricted early antigen complex," *Virology*, 160:151–161, 1987.

Pihl–Carey, "Disease drug fails in phase III," *BioWorld Today*, 10:1–2, 1999.

Potter et al., "Enhancer–dependent expression of human Λ immunoglobulin genes introduced into mouse pre–B lymphocytes by electroporation," *Proc. Nat'l Acad. Sci. USA*, 81:7161–7165, 1984.

Ridgeway, "Mammalian expression vectors," *In:* Rodriguez RL, Denhardt DT, (ed.) Vectors: a survey of molecular cloning vectors and their uses. Stoncham: Butterworth, pp. 467–492, 1988.

Rippe et al., "DNA–mediated gene trasfer into adult rat hepatocytes in primary culture," *Mol. Cell Biol.*, 10(2):689–695, 1990.

Stratford–Perricaudet and Perricaudet, "Gene transfer into animals: the promise of adenovirus," pp. 51–61, *In: Human Gene Transfer*, Eds, O. Cohen–Haguenauer and M. Boiron Editions John Libbey Exrotext, France, 1991.

Szoke and Papahadjopoulos, "Procedude for preparation of liposimes with large internal aqueous space and high capture by reverse–phase evaporation," *Proc. Nat'l Acad. Sci. U.S.A.* 75(9):4194–4198, 1978.

Temin, "Retrovirus vectors for gene transfer: Efficient integration into and expression of exogenous DNA in vertebrate cell genome," *In: Gene Transfer*, Kucherlapati (ed.), New York: Plenum Press, pp. 149–188, 1986.

Tur–Kaspa et al., "Use of electroporation to introduce biologically active foreign genes into primary rat hepatocytes," *Mol. Cell Biol.*, 6(2):716–718, 1986.

Verma et al., *Nature*, 389:238–243, 1997.

Wagner et al., "Antisense gene inhibition by pligonucleotides containing C5 propyne pyrimidines," *Science*, 260:1510–1513, 1993.

Wu and Wu, "Evidence for targeted gene delivery to Hep G2 hepatoma cells in vitro," *Biochemistry*, 27:887–892, 1988.

Wu and Wu, "Receptor–mediated in vitro gene transformations by a soluble DNA carrier system," *J. Biol. Chem.*, 262(10):4429–4432, 1987.

Yang et al., "In vivo and in vitro gene transfer to mammalian somatic cells by particle bombardment," *Proc. Nat'l Acad. Sci. USA*, 87:9568–9572, 1990.

Zelenin et al., "High–velocity mechanical DNA transfer of the chloramphenicolacetyl transferase gene into rodent liver, kidney and mammary gland cells in organ explants and in vivo," *FEBS Lett.*, 280(1):94–96, 1991.

Ziegler et al., "Induction of apoptosis in small–cell lung cancer cells by an antisense oligodeoxynucleotide targeting the Bcl–2 coding sequence," *J. Nat'l Cancer Institute*, 89(14):1027–1036, 1997.

Grever and Chabner, "Cancer Drug Discovery and Developoment," *Cancer Principles & Practice of Oncology, 5th Edition*, Lippicott–Raven Publishers, 19:385–394, 1997.

Kaneda et al., "Increased Expression of DNA cointroduced with nuclear protein in adult rat liver," *Science*, 242:375–378, 1989.

Kato et al., "Expression of hepatitis B virus surface antigen in adult rat liver," *J. Biol. Chem.*, 266:3361–3364, 1991.

Nicolau et al., "Liposomes as carriers for in vivo gene transfer and expression," *Methods in Enzymology*, 149:157–176, 1987.

Wong et al., "Appearance of β–lactamase activity in animal cells upon liposome–mediated gene transfer," *Gene*, 10:87–94, 1980.

Zon, "Pharmaceutical considerations," *Oligodeoxynucleotides*, Jack S. Cohen, Ed., CRC Press, 11:233–247, 1989.

Agris et al., "Inhibition of vesicular stomatitis virus protein synthesis and infection by sequence–specific oligodeoyribonucleosidemethylphosponates," *Biochemistry*, 25:6268–6275, 1986.

Akhtar et al., "Interactions of antisense DNA oligonucleotideanalogs with phospholipid membranes (liposomes)," *Nucleic Acids Research*, 19(20):5551–5559, 1991.

Akhtar et al., "Release of antisense oligdeoynucleotideanalogues from liposomes: implications for cellular transport and drug delivery," 128th Meeting of British Pharmaceutical Conference 1991, United Kingdom, Sep. 10–13, 1991, *J. Pharm. Pharmacol.*, 43( Suppl.):Abstract24P, 1991.

Arad et al., "Use of reconstituted sendai virus envelopes for fusion–mediated microinjection of double–stranded RNA: Inihibition of protein synthesis in interferon–treatedcells," *Biochimica et a Biophysica Acta*, 859:88–94, 1986.

Bennett et al., "Cationic lipids enhance cellular uptake and activity of phosphorothioateantisense oligonucleotides," *Molecular Pharmacology*, 41(6):1023–1033, 1992.

Boiziau et al., "Modified oligonucleotides in rabbit reticulocytes: uptake, stability and antisense properties," Biochimie, 73:1403–1408, 1991.

Branch, A., "A good antisense molecule is hard to find," *TIBS*, 23:45–49, 1998.

Budker et al., "Cell membranes as barriers for antisense constructions," *Antisense Research and Development*, 2:177–184, 1992.

Capaccioli et al., "Cationic lipids improve antisense oligonucleotideuptake and prevent degradation in cultured cells and in human serum," *Biochemical and Biophysical Research Communications*, 197(2):818–825, 1993.

Citro et al., "Chemical modification of ligands for cell receptors to introduce foreign compounds into the cells," *Colon & Rectum*, 37(2):S127–S132, 1994.

Gerwirtz et al., "Facilitating oligonucleotidedelivery: helping antisense delivery on its promise," *Proc. Natl Acad. Sci. U.S.A.*, 93:3161–3163, 1996.

Gura, "Antisense has growing pains," *Science*, 270:575–577, 1995.

International Search Report from the Patent Cooperation Treaty, Mar. 14, 1997.

Keller et al., "Synthesis and hybridization properties of oligonucleotides containing 2'–O–modified ribonucleotides," *Nucleic Acids Research*, 21(19):4499–4505, 1993.

Krieg et al., "Modification of antisense phosphodiesterolgiodeoynucleotidesby a 5' cholesteryl moiety increases cellular association and improves efficacy," *Proc. Natl Acad. Sci., USA*, 90:1048–1052, 1993.

Leonetti et al., "Antibody–targetedliposomes containing oligodeoyribonucleotidescomplementary to viral RNA selectively inhibit viral replication," *Proc. Natl Acad. Sci. USA*, 87:2448–2451, 1990.

Loke et al., "Characterization of oligonucleotide transport into living cells," *Proc. Natl Acad. Sci. USA*, 86:3474–3478, 1989.

Martiat et al., "Retrovirally transduced antisense sequences stably suppress $P210^{BCR-ABL}$ epression and inhibit the proliferation of BCR/ABL–containing cell lines," *Blood*, 81(2):502–509, 1993.

Miller et al., "Gene Transfer and antisense nucleic acid techniques," *Parasitology Today*, 10(3):92–97, 1994.

Miller, "Oligonucleosidemethylphosphonatesas antisense reagents," *Bio/Technology*, 9:358–362, Apr. 1991.

Moody et al., "Regiospecific inhibition of DNA duplication by antisense phosphate–methylated oligodeoynucleotides," *Nucleic Acids Research*, 17(12):4769–4782, 1989. (Abstract).

Renneisen et al., "Inhibition of epression of human immunodeficiency virus–1 in vitro by antibody–targetedliposomes containing antisense RNA to the env region," *The Journal of Biological Chemistry*, 265(27):16337–16342, 1990.

Rojanasakul, "Antisense oligonucleotide therapeutics: drug delivery and targeting," *Advanced Drug Delivery Reviews*, 18:115–131, 1996.

Shea et al., "Synthesis, hybridization properties and antiviral activity of lipid–oligodeoynucleotide conjugates," *Nucleic Acids Research*, 18(13):3777–3783, 1990.

Stein et al., "Antisense oligonucleotides as therapeutic agents—is the bullet really magical?," *Science*, 261:1004–1012, 1993.

Stein et al., "Oligodeoynucleotides as inhibitors of gene epression: A review," *Cancer Research*, 48(10):2635–2944, 1988.

Stull et al., "Antigene, ribozyme and aptamer nucleic acid drugs: progress and prospects, pharmaceutical research," 12(4):465–483, 1995.

Szczylik et al., Selective inhibition of leukemia cell proliferation by BCR–ABL antisense oligodeoynucleotides,,Science,253:562–565, 1991.

Taj et al., "Inhibition of $P210^{BCR/ABL}$ epression in K562 cells by electroporation with an Antisense oligonucleotide," *Leukemia and Lymphoma*, 3:201–208, 1990.

Thierry et al., "Liposomal delivery as a new approach to transport antisense oligonucleotides," *Gene Regualtion, Biology af Antisense RNA and DNA*, 1: 147–161, 1992.

Tidd et al., "Evaluation of N–ras oncogene anti–sense, sense and nonsense sequence methylphosphonateoligonucleotide analogues," *Anti–Cancer Drug Design*, 3:117–127, 1988.

Tidd et al., "Partial protection of oncogene, anti–sense oligodeoynucleotidesagainst serum nuclease degradation using terminal methylphosphonategroups," *Be. J. Cancer*, 60:343–350, 1989.

Tsuchida et al., "Iron–ligand bonding properties of synthetic iron–prophyrin complees wtih oygen transporting ability in aqueous media," *J. Chem Soc. Dalton Transactions*, 10:2455–2458, 1987.

Uhlmann et al., "Antisense oligonucleotides: a new therapeutic principal," *Chemical Reviews*, 90(4):543–584, 1990.

Vasanthakumar et al., "Modulation of drug resistance in a daunorubicin resistant subline with oligonucleoside methylphosphonates," *Cancer Communications*, 1(4):225–232, 1989.

Wagner, "Gene inhibition using antisense oligodeoynucleotides," *Nature*, 372:333–335, 1994.

Weiss, "Upping the antisense ante scientists bet on profits from reverse genetics," *Science News*, 139:108–109, 1991.

Wickstrom, "Antisense DNA therapeutics neutral analogs and their stereochemistry," *Raven Press Ser. Mol. Cell. Biol.*, 1:119–132, 1992.

Wu–Pong, "Oligonucleotides: Opportunities for drug therapy and research, pharmaceutical technology," 18:102–114, 1984.

Yeoman et al., "Lipofection enhances cellular uptake of antisense DNA while inhibiting tumor cell growth", *Antisense Research and Development*, 2:51–59, 1992.

Aktar et al., "Lipsome Delivery of Antisense Methylphosphonate and Phosphorothioate Oligonucleotides: A Study with MLV, FATMLV, and LUV Liposomes," *Proceed. Intern. Symp. Control. Rel. Bioact. Mater.,* 19:345–346, 1992.

Clarenc et al., "Delivery of Antisense Oligonucleotides by poly(L–Lysine) Conjugation and Liposome Encapsulation," *Anti–Cancer Drug Design,* 8:81–94, 1993.

Gomez–Manzano et al., "Bax, Bcl–2 and p53 Interations Modulate p53–Induced Apoptosis in Glioma Cells," *Proceedings of the American Association for Cancer Research,* 37:204, Abstract 1397, Mar. 1996.

Juliano et al., "Lipsomes as a Drug Delivery System for Antisense Oligodeoxynucleotides Encapsulated by Liposomes," *Antisense Research and Development,* 2:165–176, 1992.

Loke et al., "Delivery of *c–myc* Antisense Phosphorothioate Oligodeoxynucleotides to Hematopoietic Cells in Culture by Lipsome Fusion: Specific Reduction in *c–myc* Protein Expression Correlates with Inhibition of Cell Growth and DNA Synthesis," *Current Topics in Microbiology and Immunology, Mechanisms in B–Cell Neoplasis,* 141:282–289, 1988.

Marin et al., "Complementation and Cell Death Regulation by Bcl–2, p53 and c–myc During In Vivo Lymphomagenesis," *Journal of Cellular Biochemistry,* Supplement 19B, p 286, Abstract B8–224, Feb. 5–Mar. 15, 1995.

McDonnell et al., "Cell Death Suppression by Bcl–2 Is Associated with Altered Nuclear–Cytoplasmic Trafficking," *Proceedings of the American Association for Cancer Research,* 37:16, Abstract 111, Mar. 1996.

Ropert et al., "Inhibition of the Friend Retrovius by Antisense Oligonucleotides Encapsulated in Liposomes: Mechanism Action," *Pharmaceutical Research,* 10(10):1427–1433, Apr. 1993.

Skorski et al., "Gene–targeted Specific Inhibition of Chronic Myeloid Leukemia Cell Growth by BCR–ABL Antisense Oligodeoxynucleotides," *Folia Histochemica et Cytobiologica,* 29(3):85–90, 1991.

Tari et al., "Lipsomal Delivery of Methylphosphonate Antisense Oligodeoxynucleotides in Chronic Myelogenous Leukemia," *Blood,* 84(2):601–607, Jul. 1994.

Thierry et al., Intracellular Availability of Unmodified, Phosphorothioated and Liposomally Encapsulated Oligodeoxynucleotides for Antisense Activity, *Nucleic Acids Research,* 20(21):5691–5698, Sep. 1992.

Thierry et al. "Liposomal Delivery as a New Approach to Transport Antisense Oligonucleotides," *Gene Regulation, Biology of Antisense RNA and DNA,* 1:47–161, 1992.

Thierry et al., "Modulation of Multidrug Resistance by Antisense Oligodeoxynucleotides Encapsulated by Liposomes," *Proceedings of the American Association for Cancer, Preclinical Pharmacology/Experimental Therapeutics,* Abstract 2578, 32:443, Mar. 1991.

Thierry et al., Overcoming Multidrug Resistance in Human Tumor Cells Using Free and Liposomally Encapsulated Antisense Oligodeoxynucleotides,: *Biochemical and Biophysical Research Communications,* 190(3):952–960, Feb. 1994.

Tormo et al., "Antitumor Acivity of Liposomal–Bcl–2–Antisense Oligonucleotides in Follicular Lymphoma," *Proceedings of the American Association for Cancer Research,* 37:173, Abstract 1190, Mar. 1996.

U.S. Appl. No. 08/520,385 filed Aug. 29, 1995 Inventors G. Lopez–Berestein and A.M. Tari.

Bradbury et al., "Down–Regulation of bcl–2 in AML Blasts by All–Trans Retinoic Acid and Its Relationship of CD34 Antigen Expression," *British Journal of Haemaltology,* 94:671–675, 1996.

Capaccioli et al., "A bcl–2/IgH Antisense Transcript Deregulates bcl–2 Gene Expression in Human Follicular Lymphoma t(14;18) Cell Lines," Oncogene, 13:105–115, 1996.

Masserano et al., "Dopamine Induces Apoptotic Cell Death of a Catecholaminergic Cell Line Derived from the Central Nervous System," Molecular Pharmacology, 50:1309–1315, 1996.

Schendel et al., "Channel Formation by Antiapoptotic Protein Bcl–2," Proc. Natl. Acad. Sci. USA, 94:5113–5118, 1997.

Weber–Nordt et al., "Interleukin–10 Increases Bcl–2 Expression and Survival in Primary Human CD34+ Hematopoietic Progenitor Cells," Blood, 88(7):2549–2558, 1996.

Zhang et al., "BCL2 Regulates Neural Differentiation," Proc. Natl. Acad. Sci. USA, 93:4504–4508, 1996.

Allsopp et al., "The Proto–Oncogene bcl–2 Can Selectively Rescue Neurotrophic Factor–Dependent Neurons from Apoptosis," *Cell,* 73:295, 1993.

Bakhshi et al., "Cloning the Chromosomal Breakpoint of t(14;18) Human Lymphomas: Clustering around $J_H$ on Chromosome 14 and near a Transcriptional Unit on 18," *Cell,* 41:899, 1985.

Boise, et al., "bcl–x, a bcl–2–Related Gene That Fucntions as a Dominant Regulator of Apoptotic Cell Death", *Cell,* 74:597–608, 1993.

Borzillo et al., "*Bcl–2* Confers Growth and Survival Advantage to Interleukin 7–dependent Early Pre–B Cells Which Become Factor Independent by a Multistep Process in Culture," *Oncogene,* 7:869, 1992.

Campos et al., "Effects of *BCL–2* Antisense Oligodeoxynucleotideson In Vitro Proliferation and Survival of Normal Marrow Progenitors and Leukemic Cells," Blood, 84:595, 1994.

Cazals–Hatem et al., "Molecular Cloning and DNA Sequence Analysis of cDNA Encoding Chicken Homologue of the Bcl–2 Oncoprotein," *Biochim. Biophys. Acta,* 1132:109, 1992.

Chao, et al., "Bcl–$X_L$ and Bcl–2 Repress a Common Pathway of Cell Death," *J. Exp. Med.,* 182:821–828, 1995.

Chen et al., "Suppression of *Bcl–2* Messenger RNA Production May Mediate Apoptosis after Ionizing Radiation, Tumor Necrosis Factor α, and Ceramide," *Cancer Res.,* 55:991–994, 1995.

Chen–Levy and Cleary, "Membrane Topology of the Bcl–2 Protooncogenic Protein Demonstrated in Vitro," *J. Biol. Chem.* 265:4929, 1990.

Chen–Levy et al., "The bcl–2 Candidate Proto–Oncogene Product Is a 24–Kilodalton Integral–Membrane Protein Highly Expressed in Lymphoid Cell Lines and Lymphomas Carrying the t(14;18) Translocation," *Mol. Cell. Biol.,* 9:701, 1989.

Cheng et al., "Bax–independent inhibition of apoptosis by Bcl–$x_L$," *Nature,* 279:554–556, 1996.

Chittenden et. al, "Induction of apoptosis by the Bcl–2 homologue Bak," *Nature,* 374:733, 1995.

Choi et al., "The role of bcl-X$_L$ in CD40-mediated rescue from anti-μ-induced apoptosis in WEHI-231 B lymphoma cells," *Eur. J. Immunol.*, 25:1352–1357, 1995.

Clarke et al., "A recombinant *bcl-x$_S$* adenovirus selectively induces apoptosis in cancer cells but not in normal bone marrow cells," *Proc. Natl Acad. Sci. USA*, 92:11024–11028, 1995.

Cleary et al., "Cloning and Structural Analysis of cDNAs for *bcl-2* and a Hybrid *bcl-2*/Immunoglobulin Transcript Resulting from the t(14:18) Translation," *Cell*, 47:19, 1986.

Cuende et al., Programmed cell death by *bcl-2*-dependent and independent mechanisms in B lymphoma cells, *EMBO J.*, 12:1555–1560, 1993.

Datta et al., "Overexpression of Bcl-X$_L$ by Cytotoxic Drug Exposure Confers Resistance to Ionizing Radiation–induced Internucleosomal DNA Framgentation,"*Cell Growth & Differentiation*, 6:363–370, 1995.

Dole et al., "Bcl-X$_L$ Is Expressed in Neuroblastoma Cells and Modulates Chemotherapy–Induced Apoptosis," *Cancer Res.*, 55:2576–2582, 1995.

Duke et. al, "Morphological, biochemical and flow cytometric assays of apoptosis," *In:* Coligan et. al (eds) Current protocols in immunology, vol. 1., New York: John Wiley & sons, p 3.17.1, 1991.

Eguchi et al., "Isolation and Characterization of the Chicken *bcl-2* Gene: Expression in a Variety of Tissues Including Lymphoid and Neuronal Organs in Adult and Embryo," *Nucl. Acids. Res.*, 20:4187, 1992.

Frankowski et al., "Function and expression of the *Bcl-x* gene in the developing and adult nervous system," *NeuroReport*, 6:1917–1921, 1995.

Garcia et al., "Prevention of Programmed Cell Death of Sympathetic Neurons by the *bcl-2* Prot–Oncogene," *Science*, 258:302, 1992.

González–Garcia et al., "*bcl-x* is expressed in embryonic and postnatal neural tissues and functions to prevent neuronal cell death," *Proc. Natl Acad. Sci. USA.*, 92:4304–4308, 1995.

González–Garcia et al., "*bcl-x$_L$* is the major *bcl-x* mRNA form expressed during murine development and its product localizes to mitochondria," *Development*, 120:3033–3042, 1994.

Gottschalk et al., "Identification of immunosuppressant–induced apoptosis in a murine B–cell line and its prevention by bcl-x but not bcl-2," *Proc. Natl Acad. Sci. USA.*, 91:7350–7354, 1994.

Gottschalk et al., "The ability of Bcl-X$_L$ and Bcl-2 to prevent apoptosis can be differentially regulated," *Death and Differentiation*, 3:113–118, 1996.

Graninger et al., "Expression of bcl-2 and bcl-2-Ig fusion transcripts in normal and neoplastic cells," *J. Clin. Invest.*, 80:1512, 1987.

Grillot et al., "*bcl-x* Exhibits Regulated Expression During B Cell Development and Activation and Modulates Lymphocyte Survival in Transgenic Mice," *J. Exp. Med.*, 183:381–391, 1996.

Hockenberry et al., "Bcl-2 is an inner mitochondrial membrane protein that blocks programmed cell death," *Nature*, 348:334, 1990.

Jäättelä et al., "Bcl-x and Bcl-2 inhibit TNF and Fas–induced apoptosis and activation of phospholipase A$_2$ in breast carcinoma cells," *Oncogene*, 10:2297–2305, 1995.

Jasty et al., "*bcl-X$_L$*, A Gene Which Regulates Programmed Cell Death, Is Expressed In Neuroblastoma Tumor Cell Lines (abstract)," *Clinical Res.*, 42:416A, 1994.

Kiefer et. al, "Modulation of apoptosis by the widely distributed Bcl-2 homologue Bak," *Nature*, 374: 736, 1995.

Kitada et al., "Investigationsof antisense oligonucleotidestargeted against bcl-2 RNAs," *Antisense Res. Dev.*, 3:157, 1993.

Kozopas et al., "MCL-1, a gene expressed in programemd myeloid cell differentiation, has sequence similarity to BCL-2," *Proc. Nat'l Acad. Sci. USA*, 90:3516, 1993.

Krajewski et al., "Immunohistochemical Analysis of In Vivo Patterns of Bcl-x Expression," *Cancer Res.*, 54:5501–5507, 1994.

Kramer et al., "Self–specific T lymphocyte lines as vehicles for gene therapy: myelin specific T cells carrying exogenous nerve growth factor gene (abstract)," *J. Cell. Biochem.*, Suppl. o (17 Part E):215, 1993.

Lin et al, "Characterization of A1, a novel hemopoietic–specificearly–responsegene with sequence similarity to BCL-2," *J. Immunol.*, 151:1979, 1993.

McCarthy et al., "Apoptosis in the development of the immune system: Growth factors, clonal selection and *bcl-2*," *Cancer Metastasis Reviews*, 11:157–178, 1992.

McDonnell et. al, "Bcl-2-immunoglobulintransgenic mice demonstrate extended B cell survival and follicular lymphoproliferation," *Cell*, 57:79, 1989.

McDonnell, et al., "The bcl-2-Immunoglobulin Transgenic Mouse: A Model of the t(14;18) Translocation in Human Follicular Lymphoma," *Transgene*, 1:47, 1993.

Minn et al., "Expression of Bcl-X$_L$ can Confer a Multidrug Resistance Phenotype," *Blood*, 86:1903–1910, 1995.

Miyashita et. al, "Tumor suppressor p53 is a regulator of bcl-2 and bax gene expression in vitro and in vivo," *Oncogene*, 9:1799, 1994.

Núñez et al., "BCL-X is expressed in embryonic and adult neuronal tissues and its expression prevents neuronal cell death (abstract)," *J. Cell. Biochem.*, Supplement 0 (19B), B8–438, p. 317, 1995.

Núñez et al., "Deregulation BCL-2 gene expression selectively prolongs survival of growth factors–deprived hemopoietic cell lines," *J. Immunol.*, 144:3602, 1990.

Oltvai et al., "Bcl-2 Heterodimerizes In Vivo with a Conserved Homolog, Bax, That Accelerates Programmed Cell Death", *Cell* 74:609–619, 1993.

Oppenheim et al., "Brain–derived neurotrophic factor rescues developing avian motoneurons from cell death," *Nature*, 360:755–757, 1992.

Raff, M.C., "Social controls on cell survival and cell death," *Nature*, 356:397–400, 1992.

Reed et al., "Bcl-2-mediatedtumorigenicity in a human T–lymphoid cell line: synergy with c–myc and inhibition by Bcl-2 antisense," *Proc. Nat'l Acad. Sci. USA*, 87:3660, 1990b.

Reed et al., "Antisense–Mediated Inhibition Of BCL-2 ProtooncogeneExpression And Leukemic Cell Growth And Survival: Comparisons Of Phosphodiester and Phosphorothioate Oligodeoxynucleotides," *Cancer Res.*, 50:6565, 1990.

Reed et al., "Regulation of *bcl-2* Proto–Oncogene Expression During Normal Human Lymphocyte Proliferation," *Science*, 236:1295, 1987.

Reed, et al., "Bcl–2: prevention of apoptosis as a mechanism of drug resistance," *Hematol. Oncol. Clin. North Am.,* 9:451, 1995.

Sato et al., "Interactions among members of the Bcl–2 protein family analyzed with a yeast two–hybrid system," *Proc. Natl. Acad. Sci. USA.,* 91:9238–9242, 1994.

Schott et al., "Bcl–$X_L$ protects cancer cells from p53–mediated apoptosis," *Oncogene,* 11(7):1389–1394, 1995.

Schott, et al., "BCL–$X_L$ Protects Cells from P53–Mediated Apoptosis", *Journal of Investigative Medicine* 43(SUPPL. 3) 458A, 1995.

Sedlak et al., "Multiple Bcl–2 family members demonstrate selective dimerization with Bax," *Proc. Nat'l Acad. Sci. USA,* 92:7834, 1995.

Sentman et al., "bcl–2 Inhibits Multiple Forms of Apoptosis but Not Negative Selection in Thymocytes," *Cell,* 67:879, 1991.

Siegel et al., "Inhibition of thymocyte apoptosis and negative and antigenic selection in *bcl–2* transgenic mice," *Proc. Natl. Acad. Sci. USA,* 89:7003, 1992.

Strasser et al., "bcl–2 Transgene Inhibits T Cell Death and Perturbs Thymic Self–Censorship," *Cell,* 67:889, 1991.

Strasser et al., "Enforcer *BCL2* Expression in B–lymphoid Cells Prolongs Antibody Responses and Elicits Autoimmune Disease," *Proc. Natl. Acad. Sci. USA,* 88:8661, 1991.

Sumantran et al., "Overexpression of Bcl–$x_S$ Sensitizes MCF–7 Cells to Chemotherapy–Induced Apoptosis," *Cancer Res.,* 55:2507–2510, 1995.

Thompson, C. B., "Apoptosis in the Pathogenesis and Treatment of Disease," *Science,* 267:1456–1462, 1995.

Tormo et al., "Antitumor activity of liposomal–bcl–2– antisense oligonucleotides in follicular lymphoma (abstract)," *Proc. Am. Assoc. Cancer. Res.,* 37:1190, 1996.

Tsujimoto and Croce, "Analysis of the structure, trasncripts, and protein products of *bcl–2,* the gene involved in human follicular lymphoma," *Proc. Natl. Acad. Sci. USA,* 83:5214, 1986.

Tsujimoto et. al, "Characterization of the protein product of bcl–2, the gene involved in human follicular lymphoma," *Oncogene,* 2:3, 1987.

Tsujimoto et. al, "The t(14;18) chromosome translocation involved in B–cell neoplasms result from mistakes in VDJ joining," *Science,* 229:1390, 1985.

Vaux et al., "*Bcl–2* gene promotes haempoietic cell survival and cooperates with *c–myc* to immortalize pre–B cells," *Nature,* 335:440, 1988.

Webb et al., "Extrathymic Tolerance of Mature T Cells: Clonal Elimination as a Consequence of Immunity," *Cell,* 63:1249, 1990.

Williams, G.T., "Programmed Cell Death: Apoptosis and Oncogenesis," *Cell,* 65:1097–1098, 1991.

Wrone–Smith, et al., "Discordant Expression of Bcl–x and Bcl–2 by Keratinocytes in Vitro and Psoriatic Keratinocytes in Vivo," *Am. J. Pathology,* 146:1079–1088, 1995.

Yang et al., "Bad, a Heterodimeric Partner for Bcl–$X_L$ and Bcl–2, Displaces Bax and Promotes Cell Death," *Cell,* 80:285, 1995.

Yin et. al, "BH1 and BH2 domains of Bcl–2 are required for inhibition of apoptosis and heterodimerizationwith Bax," *Nature,* 369:321, 1994.

Zhang et al., "Gene therapy for the peripheral nervous system rat neuritogenic T cell line carry mouse nerve growth factor gene (abstract)," *J. Cell. Biochem.,* Suppl. 0 (17 Part E):SZ–116, 1993.

* cited by examiner

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:1:

CAGCGTGCGC CATCCTTC (2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

```
ACGGTCCGCC ACTCCTTCCC                                              20
```

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:3:

```
CTGAAGGGCT TCTTCC                                                  16
```

(2) INFORMATION FOR SEQ ID NO:4:

(i) SEQUENCE CHARACTERISTICS:
        (A) LENGTH: 5086 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1459..2175

(xi) SEQUENCE DESCRIPTION: SEQ ID NO:4:

```
GCGCCCGCCC CTCCGCGCCG CCTGCCCGCC CGCCCGCCGC GCTCCCGCCC GCCGCTCTCC    60

GTGGCCCCGC CGCGCTGCCG CCGCCGCCGC TGCCAGCGAA GGTGCCGGGG CTCCGGGCCC   120

TCCCTGCCGG CGGCCGTCAG CGCTCGGAGC GAACTGCGCG ACGGGAGGTC CGGGAGGCGA   180

CCGTAGTCGC GCCGCCGCGC AGGACCAGGA GGAGGAGAAA GGGTGCGCAG CCCGGAGGCG   240

GGGTGCGCCG GTGGGGTGCA GCGGAAGAGG GGGTCCAGGG GGGAGAACTT CGTAGCAGTC   300

ATCCTTTTTA GGAAAAGAGG GAAAAAATAA AACCCTCCCC CACCACCTCC TTCTCCCCAC   360

CCCTCGCCGC ACCACACACA GCGCGGGCTT CTAGCGCTCG GCACCGGCGG GCCAGGCGCG   420

TCCTGCCTTC ATTTATCCAG CAGCTTTTCG GAAAATGCAT TTGCTGTTCG GAGTTTAATC   480

AGAAGACGAT TCCTGCCTCC GTCCCCGGCT CCTTCATCGT CCCATCTCCC CTGTCTCTCT   540

CCTGGGGAGG CGTGAAGCGG TCCCGTGGAT AGAGATTCAT GCCTGTGTCC GCGCGTGTGT   600

GCGCGCGTAT AAATTGCCGA GAAGGGGAAA ACATCACAGG ACTTCTGCGA ATACCGGACT   660

GAAAATTGTA ATTCATCTGC CGCCGCCGCT GCCAAAAAAA AACTCGAGCT CTTGAGATCT   720

CCGGTTGGGA TTCCTGCGGA TTGACATTTC TGTGAAGCAG AAGTCTGGGA ATCGATCTGG   780

AAATCCTCCT AATTTTTACT CCCTCTCCCC CCGACTCCTG ATTCATTGGG AAGTTTCAAA   840

TCAGCTATAA CTGGAGAGTG CTGAAGATTG ATGGGATCGT TGCCTTATGC ATTTGTTTTG   900

GTTTTACAAA AAGGAAACTT GACAGAGGAT CATGCTGTAC TTAAAAAATA CAAGTAAGTC   960

TCGCACAGGA AATTGGTTTA ATGTAACTTT CAATGGAAAC CTTTGAGATT TTTTACTTAA  1020

AGTGCATTCG AGTAAATTTA ATTTCCAGGC AGCTTAATAC ATTGTTTTTA GCCGTGTTAC  1080

TTGTAGTGTG TATGCCCTGC TTTCACTCAG TGTGTACAGG GAAACGCACC TGATTTTTTA  1140
```

```
CTTATTAGTT TGTTTTTTCT TTAACCTTTC AGCATCACAG AGGAAGTAGA CTGATATTAA    1200

CAATACTTAC TAATAATAAC GTGCCTCATG AAATAAAGAT CCGAAAGGAA TTGGAATAAA    1260

AATTTCCTGC GTCTCATGCC AAGAGGGAAA CACCAGAATC AAGTGTTCCG CGTGATTGAA    1320

GACACCCCCT CGTCCAAGAA TGCAAAGCAC ATCCAATAAA ATAGCTGGAT TATAACTCCT    1380

CTTCTTTCTC TGGGGGCCGT GGGGTGGGAG CTGGGGCGAG AGGTGCCGTT GGCCCCCGTT    1440

GCTTTTCCTC TGGGAAGG ATG GCG CAC GCT GGG AGA ACG GGG TAC GAC AAC      1491
                    Met Ala His Ala Gly Arg Thr Gly Tyr Asp Asn
                     1               5                      10

CGG GAG ATA GTG ATG AAG TAC ATC CAT TAT AAG CTG TCG CAG AGG GGC      1539
Arg Glu Ile Val Met Lys Tyr Ile His Tyr Lys Leu Ser Gln Arg Gly
             15                  20                  25

TAC GAG TGG GAT GCG GGA GAT GTG GGC GCC GCG CCC CCG GGG GCC GCC      1587
Tyr Glu Trp Asp Ala Gly Asp Val Gly Ala Ala Pro Pro Gly Ala Ala
         30                  35                  40

CCC GCA CCG GGC ATC TTC TCC TCC CAG CCC GGG CAC ACG CCC CAT CCA      1635
Pro Ala Pro Gly Ile Phe Ser Ser Gln Pro Gly His Thr Pro His Pro
     45                  50                  55

GCC GCA TCC CGC GAC CCG GTC GCC AGG ACC TCG CCG CTG CAG ACC CCG      1683
Ala Ala Ser Arg Asp Pro Val Ala Arg Thr Ser Pro Leu Gln Thr Pro
60                  65                  70                  75

GCT GCC CCC GGC GCC GCC GCG GGG CCT GCG CTC AGC CCG GTG CCA CCT      1731
Ala Ala Pro Gly Ala Ala Ala Gly Pro Ala Leu Ser Pro Val Pro Pro
                 80                  85                  90

GTG GTC CAC CTG GCC CTC CGC CAA GCC GGC GAC GAC TTC TCC CGC CGC      1779
Val Val His Leu Ala Leu Arg Gln Ala Gly Asp Asp Phe Ser Arg Arg
             95                 100                 105

TAC CGC GGC GAC TTC GCC GAG ATG TCC AGC CAG CTG CAC CTG ACG CCC      1827
Tyr Arg Gly Asp Phe Ala Glu Met Ser Ser Gln Leu His Leu Thr Pro
         110                 115                 120

TTC ACC GCG CGG GGA CGC TTT GCC ACG GTG GTG GAG GAG CTC TTC AGG      1875
Phe Thr Ala Arg Gly Arg Phe Ala Thr Val Val Glu Glu Leu Phe Arg
125                 130                 135

GAC GGG GTG AAC TGG GGG AGG ATT GTG GCC TTC TTT GAG TTC GGT GGG      1923
Asp Gly Val Asn Trp Gly Arg Ile Val Ala Phe Phe Glu Phe Gly Gly
140                 145                 150                 155

GTC ATG TGT GTG GAG AGC GTC AAC CGG GAG ATG TCG CCC CTG GTG GAC      1971
Val Met Cys Val Glu Ser Val Asn Arg Glu Met Ser Pro Leu Val Asp
                 160                 165                 170

AAC ATC GCC CTG TGG ATG ACT GAG TAC CTG AAC CGG CAC CTG CAC ACC      2019
Asn Ile Ala Leu Trp Met Thr Glu Tyr Leu Asn Arg His Leu His Thr
             175                 180                 185

TGG ATC CAG GAT AAC GGA GGC TGG GAT GCC TTT GTG GAA CTG TAC GGC      2067
Trp Ile Gln Asp Asn Gly Gly Trp Asp Ala Phe Val Glu Leu Tyr Gly
         190                 195                 200

CCC AGC ATG CGG CCT CTG TTT GAT TTC TCC TGG CTG TCT CTG AAG ACT      2115
Pro Ser Met Arg Pro Leu Phe Asp Phe Ser Trp Leu Ser Leu Lys Thr
     205                 210                 215

CTG CTC AGT TTG GCC CTG GTG GGA GCT TGC ATC ACC CTG GGT GCC TAT      2163
Leu Leu Ser Leu Ala Leu Val Gly Ala Cys Ile Thr Leu Gly Ala Tyr
220                 225                 230                 235

CTG AGC CAC AAG TGAAGTCAAC ATGCCTGCCC CAAACAAATA TGCAAAGGT           2215
Leu Ser His Lys

TCACTAAAGC AGTAGAAATA ATATGCATTG TCAGTGATGT ACCATGAAAC AAAGCTGCAG    2275

GCTGTTTAAG AAAAAATAAC ACACATATAA ACATCACACA CACAGACAGA CACACACACA    2335

CACAACAATT AACAGTCTTC AGGCAAAACG TCGAATCAGC TATTTACTGC CAAAGGGAAA    2395
```

```
TATCATTTAT TTTTTACATT ATTAAGAAAA AAGATTTATT TATTTAAGAC AGTCCCATCA      2455

AAACTCCGTC TTTGGAAATC CGACCACTAA TTGCCAAACA CCGCTTCGTG TGGCTCCACC      2515

TGGATGTTCT GTGCCTGTAA ACATAGATTC GCTTTCCATG TTGTTGGCCG GATCACCATC     2575

TGAAGAGCAG ACGGATGGAA AAAGGACCTG ATCATTGGGG AAGCTGGCTT TCTGGCTGCT     2635

GGAGGCTGGG GAGAAGGTGT TCATTCACTT GCATTTCTTT GCCCTGGGGG CGTGATATTA     2695

ACAGAGGGAG GGTTCCCGTG GGGGAAGTC CATGCCTCCC TGGCCTGAAG AAGAGACTCT      2755

TTGCATATGA CTCACATGAT GCATACCTGG TGGGAGGAAA AGAGTTGGGA ACTTCAGATG     2815

GACCTAGTAC CCACTGAGAT TCCACGCCG AAGGACAGCG ATGGGAAAAA TGCCCTTAAA      2875

TCATAGGAAA GTATTTTTTT AAGCTACCAA TTGTGCCGAG AAAAGCATTT TAGCAATTTA    2935

TACAATATCA TCCAGTACCT TAAACCCTGA TTGTGTATAT TCATATATTT TGGATACGCA    2995

CCCCCCAACT CCCAATACTG GCTCTGTCTG AGTAAGAAAC AGAATCCTCT GGAACTTGAG    3055

GAAGTGAACA TTTCGGTGAC TTCCGATCAG GAAGGCTAGA GTTACCCAGA GCATCAGGCC    3115

GCCACAAGTG CCTGCTTTTA GGAGACCGAA GTCCGCAGAA CCTACCTGTG TCCCAGCTTG    3175

GAGGCCTGGT CCTGGAACTG AGCCGGGCCC TCACTGGCCT CCTCCAGGGA TGATCAACAG    3235

GGTAGTGTGG TCTCCGAATG TCTGGAAGCT GATGGATGGA GCTCAGAATT CCACTGTCAA    3295

GAAAGAGCAG TAGAGGGGTG TGGCTGGGCC TGTCACCCTG GGGCCCTCCA GGTAGGCCCG    3355

TTTTCACGTG GAGCATAGGA GCCACGACCC TTCTTAAGAC ATGTATCACT GTAGAGGGAA    3415

GGAACAGAGG CCCTGGGCCT TCCTATCAGA AGGACATGGT GAAGGCTGGG AACGTGAGGA    3475

GAGGCAATGG CCACGGCCCA TTTTGGCTGT AGCACATGGC ACGTTGGCTG TGTGGCCTTG    3535

GCCACCTGTG AGTTTAAAGC AAGGCTTTAA ATGACTTTGG AGAGGGTCAC AAATCCTAAA    3595

AGAAGCATTG AAGTGAGGTG TCATGGATTA ATTGACCCCT GTCTATGGAA TTACATGTAA    3655

AACATTATCT TGTCACTGTA GTTTGGTTTT ATTTGAAAAC CTGACAAAAA AAAGTTCCA    3715

GGTGTGGAAT ATGGGGGTTA TCTGTACATC CTGGGGCATT AAAAAAAAAT CAATGGTGGG    3775

GAACTATAAA GAAGTAACAA AAGAAGTGAC ATCTTCAGCA AATAAACTAG GAAATTTTTT    3835

TTTCTTCCAG TTTAGAATCA GCCTTGAAAC ATTGATGGAA TAACTCTGTG GCATTATTGC    3895

ATTATATACC ATTTATCTGT ATTAACTTTG GAATGTACTC TGTTCAATGT TTAATGCTGT    3955

GGTTGATATT TCGAAAGCTG CTTTAAAAAA ATACATGCAT CTCAGCGTTT TTTTGTTTTT    4015

AATTGTATTT AGTTATGGCC TATACACTAT TTGTGAGCAA AGGTGATCGT TTTCTGTTTG    4075

AGATTTTTAT CTCTTGATTC TTCAAAAGCA TTCTGAGAAG GTGAGATAAG CCCTGAGTCT    4135

CAGCTACCTA AGAAAAACCT GGATGTCACT GGCCACTGAG GAGCTTTGTT TCAACCAAGT    4195

CATGTGCATT TCCACGTCAA CAGAATTGTT TATTGTGACA GTTATATCTG TTGTCCCTTT    4255

GACCTTGTTT CTTGAAGGTT TCCTCGTCCC TGGGCAATTC CGCATTTAAT TCATGGTATT    4315

CAGGATTACA TGCATGTTTG GTTAAACCCA TGAGATTCAT TCAGTTAAAA ATCCAGATGG    4375

CGAATGACCA GCAGATTCAA ATCTATGGTG GTTTGACCTT TAGAGAGTTG CTTTACGTGG    4435

CCTGTTTCAA CACAGACCCA CCCAGAGCCC TCCTGCCCTC CTTCCGCGGG GGCTTTCTCA    4495

TGGCTGTCCT TCAGGGTCTT CCTGAAATGC AGTGGTCGTT ACGCTCCACC AAGAAAGCAG    4555

GAAACCTGTG GTATGAAGCC AGACCTCCCC GGCGGGCCTC AGGGAACAGA ATGATCAGAC    4615

CTTTGAATGA TTCTAATTTT TAAGCAAAAT ATTATTTTAT GAAAGGTTTA CATTGTCAAA    4675

GTGATGAATA TGGAATATCC AATCCTGTGC TGCTATCCTG CCAAAATCAT TTTAATGGAG    4735
```

```
TCAGTTTGCA GTATGCTCCA CGTGGTAAGA TCCTCCAAGC TGCTTTAGAA GTAACAATGA      4795

AGAACGTGGA CGTTTTTAAT ATAAAGCCTG TTTTGTCTTT TGTTGTTGTT CAAACGGGAT      4855

TCACAGAGTA TTTGAAAAAT GTATATATAT TAAGAGGTCA CGGGGGCTAA TTGCTAGCTG      4915

GCTGCCTTTT GCTGTGGGGT TTTGTTACCT GGTTTTAATA ACAGTAAATG TGCCCAGCCT      4975

CTTGGCCCCA GAACTGTACA GTATTGTGGC TGCACTTGCT CTAAGAGTAG TTGATGTTGC      5035

ATTTTCCTTA TTGTTAAAAA CATGTTAGAA GCAATGAATG TATATAAAAG C              5086
```

(2) INFORMATION FOR SEQ ID NO:5:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235
```

(2) INFORMATION FOR SEQ ID NO:6:

(i) SEQUENCE CHARACTERISTICS:
        (A) LENGTH: 911 base pairs
        (B) TYPE: nucleic acid
        (C) STRANDEDNESS: single
        (D) TOPOLOGY: linear (ix) FEATURE:

(A) NAME/KEY: CDS
        (B) LOCATION: 147..761

(xi) SEQUENCE DESCRIPTION: SEQ ID NO:6:

```
TGATTGAAGA CACCCCCTCG TCCAAGAATG CAAAGCACAT CCAATAAAAT AGCTGGATTA       60

TAACTCCTCT TCTTTCTCTG GGGGCCGTGG GGTGGGAGCT GGGGCGAGAG GTGCCGTTGG      120

CCCCCGTTGC TTTTCCTCTG GAAGG ATG GCG CAC GCT GGG AGA ACG GGG TAC       173
                            Met Ala His Ala Gly Arg Thr Gly Tyr
                             1               5

GAC AAC CGG GAG ATA GTG ATG AAG TAC ATC CAT TAT AAG CTG TCG CAG       221
Asp Asn Arg Glu Ile Val Met Lys Tyr Ile His Tyr Lys Leu Ser Gln
 10              15                  20                  25

AGG GGC TAC GAG TGG GAT GCG GGA GAT GTG GGC GCC GCG CCC CCG GGG       269
Arg Gly Tyr Glu Trp Asp Ala Gly Asp Val Gly Ala Ala Pro Pro Gly
                 30                  35                  40

GCC GCC CCC GCA CCG GGC ATC TTC TCC TCC CAG CCC GGG CAC ACG CCC       317
Ala Ala Pro Ala Pro Gly Ile Phe Ser Ser Gln Pro Gly His Thr Pro
             45                  50                  55

CAT CCA GCC GCA TCC CGC GAC CCG GTC GCC AGG ACC TCG CCG CTG CAG       365
His Pro Ala Ala Ser Arg Asp Pro Val Ala Arg Thr Ser Pro Leu Gln
         60                  65                  70

ACC CCG GCT GCC CCC GGC GCC GCC GCG GGG CCT GCG CTC AGC CCG GTG       413
Thr Pro Ala Ala Pro Gly Ala Ala Ala Gly Pro Ala Leu Ser Pro Val
     75                  80                  85

CCA CCT GTG GTC CAC CTG GCC CTC CGC CAA GCC GGC GAC GAC TTC TCC       461
Pro Pro Val Val His Leu Ala Leu Arg Gln Ala Gly Asp Asp Phe Ser
 90                  95                 100                 105

CGC CGC TAC CGC GGC GAC TTC GCC GAG ATG TCC AGC CAG CTG CAC CTG       509
Arg Arg Tyr Arg Gly Asp Phe Ala Glu Met Ser Ser Gln Leu His Leu
                110                 115                 120

ACG CCC TTC ACC GCG CGG GGA CGC TTT GCC ACG GTG GTG GAG GAG CTC       557
Thr Pro Phe Thr Ala Arg Gly Arg Phe Ala Thr Val Val Glu Glu Leu
            125                 130                 135

TTC AGG GAC GGG GTG AAC TGG GGG AGG ATT GTG GCC TTC TTT GAG TTC       605
Phe Arg Asp Gly Val Asn Trp Gly Arg Ile Val Ala Phe Phe Glu Phe
        140                 145                 150

GGT GGG GTC ATG TGT GTG GAG AGC GTC AAC CGG GAG ATG TCG CCC CTG       653
Gly Gly Val Met Cys Val Glu Ser Val Asn Arg Glu Met Ser Pro Leu
    155                 160                 165

GTG GAC AAC ATC GCC CTG TGG ATG ACT GAG TAC CTG AAC CGG CAC CTG       701
Val Asp Asn Ile Ala Leu Trp Met Thr Glu Tyr Leu Asn Arg His Leu
170                 175                 180                 185

CAC ACC TGG ATC CAG GAT AAC GGA GGC TGG GTA GGT GCA TCT GGT GAT       749
His Thr Trp Ile Gln Asp Asn Gly Gly Trp Val Gly Ala Ser Gly Asp
                190                 195                 200

GTG AGT CTG GGC TGAGGCCACA GGTCCGAGAT CGGGGGTTGG AGTGCGGGTG           801
Val Ser Leu Gly
            205

GGCTCCTGGG CAATGGGAGG CTGTGGAGCC GGCGAAATAA AATCAGAGTT GTTGCTTCCC      861

GGCGTGTCCC TACCTCCTCC TCTGGACAAA GCGTTCACTC CCAACCTGAC                 911
```

(2) INFORMATION FOR SEQ ID NO:7:

(i) SEQUENCE CHARACTERISTICS:
        (A) LENGTH: 205 amino acids
        (B) TYPE: amino acid
        (D) TOPOLOGY: linear (ii) MOLECULE TYPE: protein -continued

```
(xi) SEQUENCE DESCRIPTION: SEQ ID NO:7:

Met Ala His Ala Gly Arg Thr Gly Tyr Asp Asn Arg Glu Ile Val Met
  1           5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
             35                  40                  45

Phe Ser Ser Gln Pro Gly His Thr Pro His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Ala
                 85                  90                  95

Leu Arg Gln Ala Gly Asp Asp Phe Ser Arg Arg Tyr Arg Gly Asp Phe
                100                 105                 110

Ala Glu Met Ser Ser Gln Leu His Leu Thr Pro Phe Thr Ala Arg Gly
                115                 120                 125

Arg Phe Ala Thr Val Val Glu Glu Leu Phe Arg Asp Gly Val Asn Trp
            130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                    165                 170                 175

Met Thr Glu Tyr Leu Asn Arg His Leu His Thr Trp Ile Gln Asp Asn
                180                 185                 190

Gly Gly Trp Val Gly Ala Ser Gly Asp Val Ser Leu Gly
            195                 200                 205
```

INHIBITION OF BCL-2 PROTEIN EXPRESSION BY LIPOSOMAL ANTISENSE OLIGODEOXYNUCLEOTIDES

BACKGROUND OF THE INVENTION

A. Field of the Invention

The present invention relates to the field of cancer therapy, specifically, the treatment of follicular lymphoma. More particularly, these treatments involve the use of antisense oligodeoxynucleotides and liposomal formulations thereof.

B. Related Art

Bcl-2 has been linked to a wide variety of diseases such as hematologic malignancies, both leukemias and lymphomas, including follicular and nonfollicular lymphomas, chronic lymphocytic leukemia, and plasma cell dyscrasias (Campos et al., 1994); solid tumors like those associated with breast, prostate and colon cancer; and immune disorders. One particular Bcl-2-related disease is Follicular non-Hodgkin Lymphoma (FL). FL is the most common lymphoid malignancy in Europe and the United States. Typically it is an indolent, low grade disease consisting of an accumulation of small, resting B cells. Although the response to chemotherapy is initially good, relapses are inevitable with the transformation to a more aggressive histological type and the development of drug resistance (Aisenberg, 1995; Johnson et. al, 1995). In over 90% of FL patients, a t(14;18) translocation is found, which results in the juxtaposition of the bcl-2 gene from chromosome 18q21 with the immunoglobulin heavy chain gene locus on chromosome 14q323 (Tsujimoto et. al, 1985; Graninger et. al, 1987). As a consequence, the bcl-2 gene is under the influence of immunoglobulin heavy chain enhancer, and the Bcl-2 protein is overexpressed (Bakhshi et. al, 1985; Tsujimoto et. al, 1987). Bcl-2 tumorigenic potential is related to its capacity of interfering with physiological death responses, thereby enhancing the longevity of the cell (Nuñez et. al, 1990). The Bcl-2 protein blocks apoptotic stimuli such as growth factor deprivation, radiation, heat-shock, virus, and most of the chemotherapeutic agents (Reed, 1995; Hockenbery et. al, 1990). In bcl-2-Ig-transgenic mice, a polyclonal follicular lymphoproliferation consisting of an expansion of mature B lymphocytes is initially observed (McDonnell et. al, 1989). Subsequently, a monoclonal high grade large immunoblastic type lymphomas develop with 50% of them presenting rearrangement of C-MYC. This suggests that a second genetic alteration is necessary for the development and progression of malignant lymphoma (McDonnell and Korsmeyer, 1991).

Recently, an expanding family of Bcl-2-related proteins has been identified. This includes Bax, Bcl-$X_L$, Bcl-$X_S$, Bad, Bak, Mcl-1, A-1, and several open reading frames in DNA viruses (Oltvai et. al, 1993; Boise et. al, 1993; Yang et. al, 1995; Chittenden et. al, 1995; Kiefer et. al, 95; Kozopas et. al, 1993; Lin et. al, 1993; Pearson et. al, 1987; Neilan et. al, 1993). Membership in the Bcl-2 family of proteins is principally defined by homology within the BH1 and BH2 domains, which help regulate dimerization between the members (Sato et. al, 1994). Bax, which shares 21% amino-acid identity with Bcl-2, can bind to Bcl-2 protein and neutralize its ability to block cell death. Thus, the ratio of Bcl-2 to Bax is thought to determine the cell's susceptibility to death following an apoptotic stimulus (Oltvai et. al, 1993; Yin et. al, 1994).

Phosphodiester antisense oligodeoxynucleotides complementary to specific sequences of the translation-initiation site of Bcl-2 mRNA are able to inhibit the production of the Bcl-2 protein and the growth of t(4;18) translocation bearing cells (Kitada et. al, 1993). However, the therapeutic use of antisense oligonucleotides has been hampered by their low cellular uptake and their rapid degradation by nucleases and other serum or cellular components. Phosphorothioate oligonucleotides, which are resistant to nuclease degradation, were found to inhibit FL cell growth at concentrations 10 times lower than phosphodiester oligonucleotides (Reed et. al, 1990a; Cotter et. al, 1994). However, this approach suffers from low cellular uptake of the oligonucleotides. For example, Reed et. al had to use concentrations of greater than 25 $\mu$M of phosphorothioates to achieve 50% growth inhibitions of cell lines derived from B-cell lymphomas, such as 697 and Su-Dhl-4 cells. Liposomal incorporation has led to enhanced uptake of oligonucleotides into leukemic cells (Akhtar et. al, 1991; Tari et. al, 1994). The use of cationic lipids by Reed et. al to deliver phosphorothioate antisense oligonucleotides allowed them to reduce the concentration of oligonucleotides to 0.075 to 0.3 $\mu$M and still induce growth inhibition in Su-Dhl-4 cells. However, there has been no reported use of liposomes to deliver Bcl-2 antisense oligonucleotides and no proof of this as a method of treating Bcl-2 mediated disease.

There is, therefore, a great need for methods and compositions for the treatment of Bcl-2 associated diseases such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

SUMMARY OF THE INVENTION

The present invention is designed to overcome the shortcomings of the prior art by providing improved compositions and methods for the treatment of Bcl-2 associated diseases, such as FL, using novel antisense oligonucleotides to target specific nucleic acids in the cells of patients.

Thus, in one embodiment, there is provided a composition comprising a polynucleotide that hybridizes to a Bcl-2-encoding polynucleotide. These polynucleotides may be oligonucleotides having a length of 8–50 bases. In a further embodiment, the polynucleotide hybridizes to the translation initiation site of Bcl-2 mRNA. In certain specific embodiments, the polynucleotide may be an oligonucleotide having the sequence $^{5'}$CAGCGTGCGCCATCCTTC$^{3'}$ (SEQ ID NO:1). In another embodiment, the polynucleotide is associated with a lipid. A polynucleotide associated with a lipid may be encapsulated in the aqueous interior of a liposome, interspersed within the lipid bilayer of a liposome, attached to a liposome via a linking molecule that is associated with both the liposome and the polynucleotide, complexed with a lipid, dispersed in a solution containing a lipid, mixed with a lipid, combined with a lipid, contained as a suspension in a lipid, contained or complexed with a micelle, or otherwise associated with a lipid.

The term "lipids" as used in this specification and the claims denotes any form of both naturally occurring and synthetic lipids or liposomes. They are fatty substances and are well-known by those of skill in the art. The lipids of the present invention are not limited to any particular structure in solution. For example, they may be present in a bilayer structure, as micelles, or with a "collapsed" structure. They may also simply be interspersed in a solution, possibly forming aggregates which are not uniform in either size or shape. The lipid may advantageously be comprised of the lipid dioleoylphosphatidylcholine, however other lipids such as other phosphatidylcholines, phosphatidylglycerols, and phosphatidylethanolamines may also be employed.

In yet another embodiment, there is provided a composition comprising a polynucleotide that hybridizes to a Bcl-2-encoding polynucleotide.

In still yet another embodiment, there is provided a composition comprising an expression construct that encodes a polynucleotide that hybridizes to a Bcl-2-encoding polynucleotide, wherein said first polynucleotide is under the control of a promoter that is active in eukaryotic cells.

This invention also comprises a method for inhibiting proliferation of a cancer cell comprising contacting said cancer cell with a composition comprising at least a polynucleotide that hybridizes to a Bcl-2-encoding nucleic acid. This method may be applied advantageously to a cancer cell that is a lymphoma cell or, more specifically, a follicular lymphoma cell. The composition may comprise a lipid which is associated with the polynucleotide, such as a polynucleotide encapsulated in a liposome. In a specific embodiment, the contacting takes place in a patient. The patient may be a human. The composition may advantageously be delivered to a human patient in a volume of 0.50–10.0 ml per dose or in an amount of 5–30 mg polynucleotide per $m^2$. In a particular regimen, the composition is administered 3 times per week for 8 weeks.

This invention relates to antisense technology that may be employed to treat Bcl-2-associated disease. In one embodiment it encompasses a composition comprising a polynucleotide that hybridizes to a Bcl-2-encoding polynucleotide and a lipid associated with the polynucleotide. The polynucleotide may be an oligonucleotide having a length of between about 8 and about 50 bases. However, oligonucleotides of other lengths may also be useful. The polynucleotide may also hybridize to the translation initiation site of Bcl-2 mRNA. An example of a useful polynucleotide is an oligonucleotide comprising the sequence CAGCGTGCGC-CATCCTTC (SEQ ID NO:1).

Compositions of the present invention also include compositions wherein liposomes are formed from the lipid. In some cases, it may be useful to have a composition in which the polynucleotide is encapsulated in the liposome. Lipids that are useful in the present invention include phosphatidylcholines, phosphatidylglycerols, and phosphatidylethanolamines, one example being the lipid dioleoylphosphatidylcholine.

An embodiment of this invention is a composition comprising an expression construct that encodes a polynucleotide that hybridizes to a Bcl-2-encoding polynucleotide, wherein said polynucleotide is under the control of a promoter that is active in eukaryotic cells.

Another embodiment encompasses a method of inhibiting a Bcl-2-associated disease comprising obtaining a polynucleotide that hybridizes to a Bcl-2-encoding polynucleotide, mixing the polynucleotide with a lipid to form a polynucleotide/lipid association, and administering said association to a cell. The cell may be a cancer cell, such as a follicular lymphoma cell. This method may employ a polynucleotide comprising an oligonucleotide having a length of between about 8 and about 50 bases. The lipid may form a comprising a liposome. If so, the liposome may further encapsulate the polynucleotide.

This embodiment also includes methods wherein the contacting takes place in an animal, such as a human. For example, the composition may be delivered to said human in a volume of 0.50–10.0 ml per dose or in an amount of from about 5 to about 30 mg polynucleotide per $m^2$. It may also be administered three times per week for eight weeks.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 4A: $1\times10^5$ Johnson cells/mL in 3 mL were treated with 3 and 4 $\mu$mol/L of L-bcl-2 or L-control oligos. After 3 days of culture, protein-containing lysates were prepared and 5 $\mu$g of total protein were subjected to SDS-PAGE and transferred to nitrocellulose membranes. Blots were cut into sections and incubated with antibodies specific for either Bcl-2 or Actin (left). To estimate the inhibition of bcl-2 protein, data were quantified by scanning densitometry and expressed as ratio of Bcl-2:Actin (right). L-bcl-2:(■); L-control:(▥).

FIG. 4B: $1\times10^5$ Jurkat cells/mL in 3 mL were treated with 3 and 4 $\mu$mol/L of L-bcl-2 or L-control oligonucleotides. After 3 days of culture, protein-containing lysates were prepared and 20 $\mu$g of total protein were subjected to SDS-PAGE and transferred to nitrocellulose membranes. Blots were cut into sections and incubated with antibodies specific for either Bcl-2 or Actin (left). To estimate the inhibition of bcl-2 protein, data were quantified by scanning densitometry and expressed as ratio of Bcl-2:Actin (right). L-bcl-2:(■); L-control:(▥).

FIG. 6A: $1 \times 10^5$ Johnson cells/mL in 3 mL were treated with 2, 3 and 4 µmol/L of L-bcl-2 or L-control oligos. After 3 days of culture, protein-containing lysates were subjected to SDS-PAGE and transferred to nitrocellulose membranes. Blots were cut into sections, and incubated with antibodies specific for either Bax or Actin. This experiment was made using the same lysates obtained in the experiment shown in FIG. 4A and FIG. 4B.

FIG. 6B: Data were quantified by scanning densitometry and expressed as ratio of Bcl-2:Bax. L-bcl-2:(-■-); L-controloligo:(-○-).

FIG. 8A: Fluorescent photograph of Johnson cells dyed with the DNA-binding dye, acridine orange, after 3 days of incubation with 5 µmol/L of L-bcl-2 (right) or without liposomal oligonucleotides ("L-OS") (left).

FIG. 8B: Apoptotic index of Johnson cells treated with 4 and 5 µM of L-bcl-2 (■), L-control oligo (▨) or empty liposomes (■). Apoptotic index=(total no. of cells with apoptotic nuclei/total no. of cell counted) ×100%.

Figure 1A:
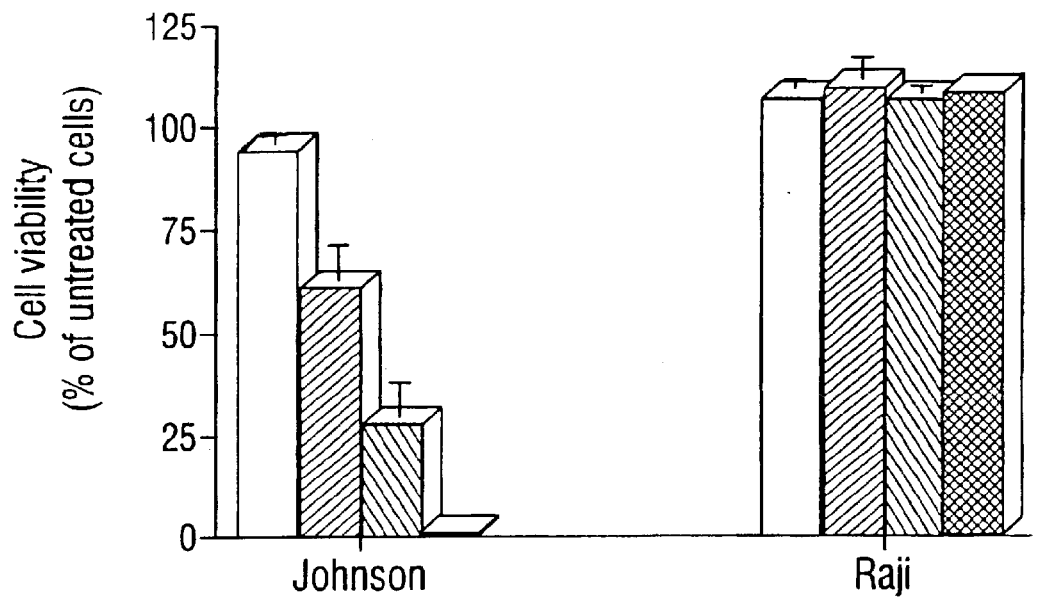
FIG. 1: Growth inhibition of lymphoid cells by liposomal-bcl-2-antisense oligonucleotides ("L-bcl-2"). Final concentrations of 3 $\mu$mol/L (▨), 4 $\mu$mol/L (▤), 5 $\mu$mol/L (▥) and 6 $\mu$mol/L (▧) of L-bcl-2 were added to Johnson, Jurkat, Raji and Daudi cells. After 5 days, the viability of the tumoral cells was measured by alamarBlue dye. Viability was expressed as percent of untreated cells.

DETAILED DESCRIPTION OF THE PREFERRED EMBODIMENTS bcl-2 is an oncogene with tumorigenic potential due to its capacity to block programmed cell death. The present invention employs liposomal antisense oligodeoxynucleotides to inhibit the production of Bcl-2 so that tumor cells can regain the capacity to enter programmed cell death. The present invention may also be used to treat hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders, which are associated with Bcl-2 expression.

The present invention relates to antisense oligonucleotides and polynucleotides directed to portions of the bcl-2 gene and their use in the treatment of Bcl-2 related diseases. A specific type of cancer that may be treated by the methods of the presents of the present invention is FL. Over 90% of follicular lymphoma patients have at(14;18) translocation which results in the translocation of the bcl-2 gene from its normal location in chromosome 18 to the immunoglobulin heavy chain gene locus on chromosome 14. In consequence, the bcl-2 gene is under the influence of the immunoglobulin heavy chain enhancer, and the Bcl-2 protein is overexpressed. Since bcl-2 is an oncogene with tumorigenic potential due to its capacity to block programmed cell death, a potential therapy for these follicular lymphomas is to inhibit the production of the Bcl-2 protein. The present invention hopes to succeed where other approaches have failed by incorporating antisense oligonucleotides specific for the translation initiation site of the Bcl-2 mRNA into liposomes to inhibit the production of Bcl-2 protein.

In particular, it is contemplated that by using these antisense molecules, either alone or in conjunction with other antisense molecules, it is possible to effectively treat FL, and possibly other cancers. For example, this invention teaches that liposomal bcl-2 antisense oligonucleotides (L-bcl-2) inhibit the growth of FL cells and in others cells which overexpress Bcl-2 protein. The oligo- or polynucleotides themselves, or expression vectors encoding therefor, may be employed. The preferred method of delivering these nucleic acids is via liposomes. The invention, in its various embodiments, is described in greater detail, below.

A. Polynucleotides and Oligonucleotides

The term "antisense" is intended to refer to polynucleotide molecules complementary to a portion of a Bcl-2 RNA, or the DNA's corresponding thereto. "Complementary" polynucleotides are those which are capable of basepairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mM (10 mM Na$^+$; 150 mM K$^+$). The intracellular concentration of divalent cation is approximately 20 mM (18 mM Mg$^+$; 2 mM Ca$^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide for thirteen or fourteen positions out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The polynucleotides according to the present invention may encode a bcl-2 gene or a portion of that gene that is sufficient to effect antisense inhibition of protein expression. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense polynucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The DNA and protein sequences for Bcl-2 are published in literature by Tsujimoto and Croce (1986) (SEQ ID NO:4, SEQ ID NO:5, SEQ ID NO:6, & SEQ ID NO:7) which is incorporated herein by reference. It is contemplated that natural variants of Bcl-2 exist that have different sequences than those disclosed herein. Thus, the present invention is not limited to use of the provided polynucleotide sequence for Bcl-2 but, rather, includes use of any naturally-occurring variants. Depending on the particular sequence of such variants, they may provide additional advantages in terms of target selectivity, i e., avoid unwanted antisense inhibition of related transcripts. The present invention also encompasses chemically synthesized mutants of these sequences.

As stated above, although the antisense sequences may be full length genomic or cDNA copies, or large fragments thereof, they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45 or 50 base pairs or larger may be used. While all or part of the gene sequence may be employed in the context of antisense construction, statistically, any sequence of 17 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone.

Alternatively, the antisense oligo- and polynucleotides of the present invention may be provided as mRNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescrip™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an antisense oligo- or polynucleotide can be optimized. Further, selection of a promoter that is regulated in response to specific physiologic signals can permit inducible expression of an inhibitory protein. For example, a nucleic acid under control of the human PAI-1 promoter results in expression inducible by tumor necrosis factor. Tables 1 and 2 list several elements/promoters which may be employed, in the context of the present invention, to regulate the expression of antisense constructs. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding an NF-IL6 inhibitory peptide in an expression construct (Table 1 and Table 2). Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
| --- | --- |
| MT II | Phorbol Ester (TPA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester (TPA) |
| Tumor Necrosis Factor | PHA |
| Thyroid Stimulating Hormone α Gene | Thyroid Hormone |

In certain embodiments of this invention, the delivery of a nucleic acid in a cell may be identified in vitro or in vivo by including a marker in the expression construct. The marker would result in an identifiable change to the transfected cell permitting easy identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. Examples include the SV40, globin or adenovirus polyadenylation signals. Also contemplated as an element of the expression cassette is a terminator. These elements can serve to enhance message levels and to minimize read through from the cassette into other sequences.

B. Lipid Formulations

In a preferred embodiment of the invention, the antisense oligo- or polynucleotides and expression vectors may be associated with a lipid. A polynucleotide associated with a lipid may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/oligonucleotide associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemaglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

Phospholipids are used for preparing the liposomes according to the present invention and can carry a net positive charge, a net negative charge or are neutral. Diacetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about $-20°$ C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately $40°$ C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

P-ethoxy oligonucleotides, nucleases resistant analogues of phosphodiesters, are preferred because they are stable in serum and effectively transported into the cellular cytoplasm. In a preferred embodiment, the lipid dioleoylphosphatidylcholine is employed. However other lipids such as other phosphatidylcholines, phosphatidylglycerols, and phosphatidylethanolamines may also be useful. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

C. Alternative Delivery Systems

Retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a Bcl-2 antisense construct is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing an inserted DNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Adenoviruses: Human adenoviruses are double-stranded DNA tumor viruses with genome sizes of approximate 36 kB. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans.

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Surprisingly persistent expression of transgenes following adenoviral infection has also been reported.

Other Viral Vectors as Expression Constructs. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedman et al, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Methods. Several non-viral methods for the transfer of expression vectors into cultured mammalian cells also are contemplated by the present invention. These include calcium phosphate precipitation (Graham and van der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fecheimer et al., 1987), gene bombardment using high velocity microprojectiles (Yang et al., 1990), polycations and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an Bcl-2 construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a Bcl-2 construct may be delivered via this method.

D. Pharmaceutical Compositions and Routes of Administration

Where clinical application of liposomes containing antisense oligo- or polynucleotides or expression vectors is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense expression vector encapsulated in a liposome as discussed above, further dispersed in pharmaceutically acceptable carrier or aqueous medium. Such compositions also are referred to as inocula. The phrases "pharmaceutically" or "pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for the treatment of skin cancers, to prevent chemotherapy-induced alopecia or other dermal hyperproliferative disorder. Alternatively, administration may be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting the dose include the physical and clinical state of the patient, the route of administration, the intended goal of treatment (alleviation of symptoms versus cure) and the potency, stability and toxicity of the particular therapeutic substance. For the instant application, it is envisioned that the amount of therapeutic peptide included in a unit dose will range from about 5–30 mg of polynucleotide.

E. Examples

EXAMPLE 1

Synthesis of Oligonucleotides

Nuclease-resistant p-ethoxy oligonucleotides, non-ionic phosphodiester analogs, were purchased from Oligo Therapeutics (Willsonville, Oreg.). An oligonucleotide specific for the translation initiation site of human Bcl-2 mRNA: 5' CAG CGTGCGCCATCCTTC3' (SEQ ID NO:1) was used as antisense oligonucleotide. Two different control oligonucleotides were used: 5' ACGGTCCGCCACTCCTTCCC3' (SEQ ID NO:2) (scrambled version of Bcl-2 antisense oligonucleotide) and the random sequence 5' CTGAAGGGCTTCTTCC3' (SEQ ID NO:3).

EXAMPLE 2

Preparation of Liposomal Oligonucleotides (L-OS)

P-ethoxy-oligonucleotides dissolved in distilled water were added to phospholipids (Avanti Polar Lipids, Alabaster, Ala.) in the presence of excess tert-butanol. The mixture was frozen in a dry ice/acetone bath, lyophilized overnight and finally hydrated with HEPES buffered saline (1 mmol/L Hepes and 10 mmol/L NaCl) at a final oligonucleotide concentration of 0.1 mmol/L. Liposomal oligonucleotides (L-OS) were sonicated for 12 minutes in a bath-type sonicator. The average diameter of the particles was 100 nm±50 nm as determined in a NICOMP particle sizing system (Santa Barbara, Calif.).

EXAMPLE 3

Oligonucleotide Inhibition of Protein Expression

Cell Lines

Johnson cells, a human transformed FL cell line bearing the t(14;18) translocation which overexpresses Bcl-2 protein, were used. Raji and Jurkat cells, a human Burkitt lymphoma cell line and a human acute T cell leukemia cell line, respectively, were also used. Both lines express the Bcl-2 protein but they lack the t(14;18) translocation. Daudi cells, a human Burkitt lymphoma cell line which does not express the Bcl-2 protein, was used as a negative control cell line. Johnson, Raji and Jurkat cells were grown in RPMI 1640 media (GIBCO, Grand Island, N.Y.) supplemented with 10% heat-inactivated fetal bovine serum (FBS). Daudi cells were grown in RPMI 1640 media supplemented with 20% heat-inactivated FBS.

Delivery of L-OS to Cells

Ten thousand cells/well were seeded in a 96-well plate in 0.1 mL of the respective medium. Cells were incubated with L-OS at final concentration of 2 to 8 μmol/L at 37° C. in a 5% $CO_2$ incubator. Each experiment was done in triplicate and repeated at least 3 times.

Cell Viability Assay

The viability of the neoplastic cells was measured by the alamarBlue dye (Alamar, Sacramento, Calif.). After 5 days of incubation with L-OS, 40 μL of cells/well were aliquoted and added to 140 μL of fresh medium. Twenty μL of alamarBlue dye were added to each well. After incubation for 12 hours at 37° C., the plates were read directly on a microplate reader (Molecular Devices, CA) at 570 and 595 nm. The difference in absorbance between 570 and 595 nm was taken as the overall absorbance value of the cells. All experiments were analyzed by t-test in which the viabilities of the cells treated with the L-OS were compared with those of the untreated controls.

Western Blots for Bcl-2 and Bax Protein

One hundred thousand cells/well were seeded in a 6-well plate in 3 mL of the respective medium, treated with 2, 3 and 4 μmol/L of L-OS and incubated at 37° C. Untreated cells were also maintained in culture. Samples were removed on day 3 after the addition of the L-OS and lysed in 100 μL of lysis buffer (1% Triton, 150 mmol/L NaCl and 25 mmol/L Tris pH 7.4) at 0° C. for 30 minutes. After centrifugation at 12,000×g for 10 minutes, the supernatants were recovered and normalized for total protein content (5 μg/lane of Johnson cells lysate and 20 μg/lane of Jurkat cells lysate for Bcl-2 analysis, and 25 μg/lane of Johnson cells for Bax analysis). The lysates were mixed with sample buffer containing 1% of sodium dodecyl sulfate (SDS) and 1% 2β-mercaptoethanol and boiled for 5 minutes. SDS-PAGE was run on 10% polyacrylamide gels, electrophoretically transferred to nitrocellulose membranes and blocked in 10% non-fat dry milk. Filters were cut in 2 portions: the bottom section was incubated with the 6C8 hamster anti-human-Bcl-2 monoclonal antibody or rabbit anti-human-Bax polyclonal antibody (Hockenbery et al), and the top section was incubated with mouse anti-actin monoclonal antibody (Amersham) at room temperature for 2 hours. After washing and incubation with a peroxidase-labeled antihamster (Kirkegaar & Perry laboratories), antirabbit (Santa Cruz) or antimouse (Amersham) secondary antibody, blots were developed by enhanced chemiluminescence system (ECL, Amersham). To estimate the inhibition of Bcl-2 protein and the ratio of Bcl-2/Bax proteins, densitometric scans were performed on western blots on a Gilford Response Gel Scanner (CIBA Coming, Medfield, Mass.). Area integration of absorbance peaks at 500 nm was used to determine the ratio of Bcl-2:Actin and Bcl-2:Bax proteins.

Analysis of Apoptosis

To qualitatively determine the internucleosomal DNA cleavage associated with apoptosis, DNA fragmentation analysis by agarose gel electrophoresis was performed (Duke et. al, 1991). In brief, $1\times10^6$ Johnson cells were cultured in 10 mL of medium in a 75 sq. cm tissue culture flask, treated with 4 μmol/L of L-OS, and incubated at 37° C. Untreated cells were also maintained in culture. Samples were removed on day 3 after treatment, washed in PBS and pellet by centrifuging 10 minutes at 200×g. The pellets were lysed in 0.5 mL of lysis buffer (10 mmol/L Tris pH 7.4, 1 mmol/L EDTA pH 8.0 and 0.2% Triton X-100) and fragmented DNA were separated from intact chromatin by microcentrifuging for 10 minutes at 13,000×g. DNA of the supernatants was precipitated in 0.7 mL ice-cold isopropanol overnight at −20° C., resuspended in 30 μL of TE buffer (10 mmol/L Tris pH 7.4, 1 mmol/L EDTA pH 8.0) and incubated in 10 μL of RNase (10 μg/mL solution) at 60° C. for 1 hour. Twenty μL of sample per well were electrophoresed on a 2% agarose gel and visualized by ethidium bromide staining.

To quantitatively determine the extent of apoptosis, we used the fluorescent DNA-binding dye acridine orange (Duke et. al, 1991). Briefly, 5 μmol/L final concentration of L-OS were added to $1\times10^5$ cells/well plated in a 24-well plate in 1 mL of medium. After 3 days of incubation at 37° C., the cells were washed with PBS and resuspended at $1\times10^6$ cells/mL. Twenty-five μL of cell suspension were mixed with 1 μL of acridine orange dye (100 μg/mL, Sigma Chemicals, St. Louis, Mo.) and observed in a fluorescent microscope. The percentage of apoptotic cells (apoptotic index) was obtained using a hemocytometer. Apoptotic index=(total no. of cells with apoptotic nuclei/total no. of cells counted)×100%.

Figure 1B:
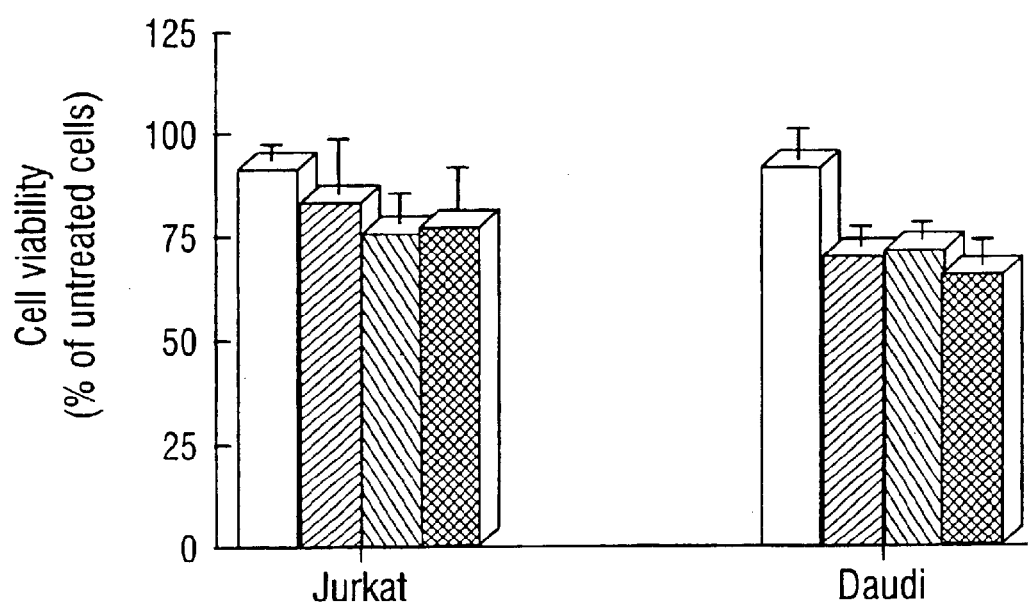

Effect of L-bcl-2-Antisense Oligonucleotides ("L-bcl-2") on Lymphoma Cell Growth Five days after the addition of L-bcl-2 to the cells, the viability of tumoral cells was assessed. Cell growth was inhibited in a concentration-dependent manner in Johnson cells, which bear the t(14;18) translocation and express very high levels of Bcl-2. A concentration of 6 μmol/L L-bcl-2 resulted in complete loss of viability of Johnson cells within 5 days (FIG. 1). Similar dose-dependent decrease in cell viabilities could be seen in three separate experiments. In contrast, after treatment with 6 μmol/L( )L-bcl-2, the viabilities of Jurkat, Raji and Daudi cells decreased by only 23%, 0% and 35%, respectively (FIG. 1).

Figure 2A:
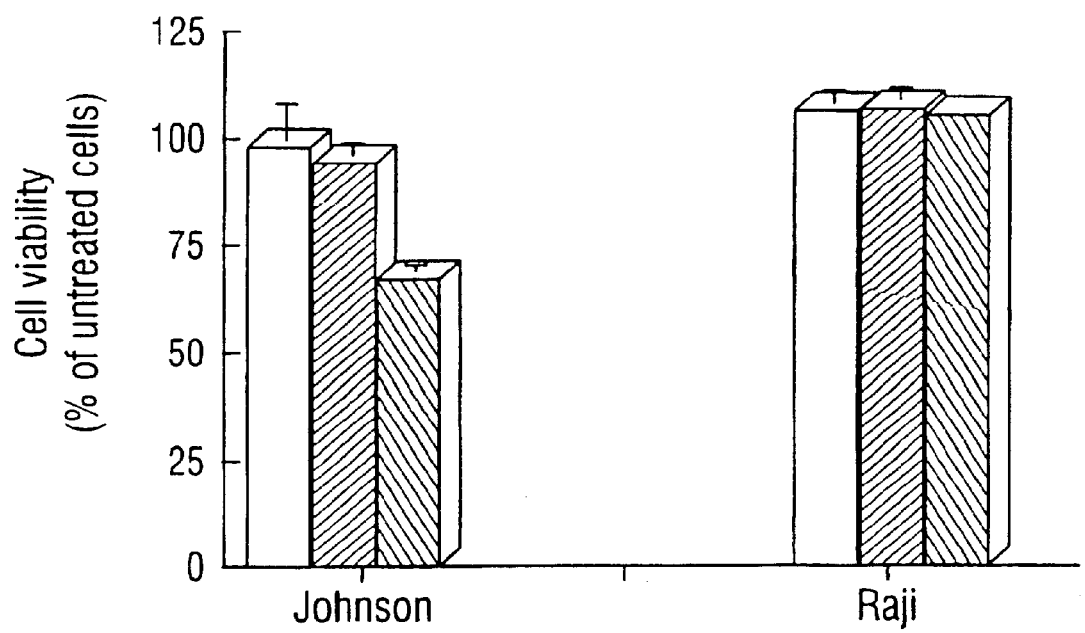
FIG. 2: Non-specific toxicity in lymphoid cells at 6 $\mu$mol/L of liposomal oligonucleotides. Empty liposomes (▧) and two different liposomal control oligonucleotides ("L-control oligos") (▨), (■) were added to Johnson, Jurkat, Raji and Daudi cells at 6 $\mu$mol/L final concentration. After 5 days, the viability of the tumoral cells was measured by alamar blue dye. Viability was expressed as percent of untreated cells.
Figure 2B:
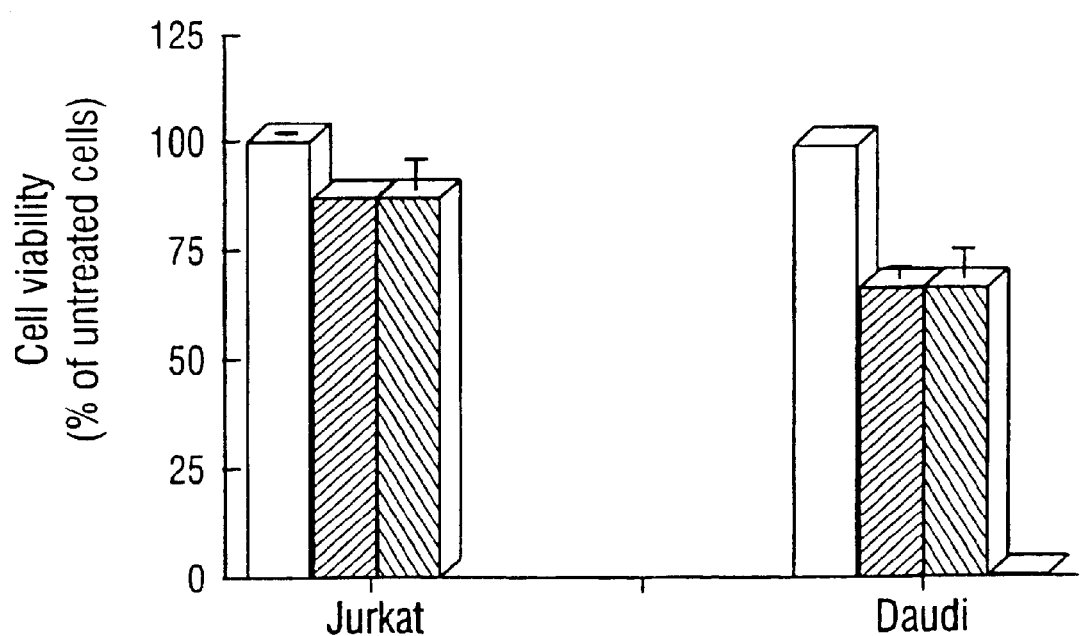

Effect of Liposomal Control Oligonucleotides (L-control Oligos) on Lymphoma Cell Growth Two control oligonucleotides were used to determine the specificity of the inhibition observed. When L-control oligos or empty liposomes were added to Johnson cells, cell growth inhibition was not observed. Jurkat, Raji and Daudi cells were also treated with L-control oligos and empty liposomes. Non-specific toxicity could be observed when greater than 6 μmol/L of L-OS were used, but not with empty liposomes (FIG. 2).

Selective Inhibition of Bcl-2 Protein by L-bcl-2-Antisense Oligonucleotides

Figure 3:
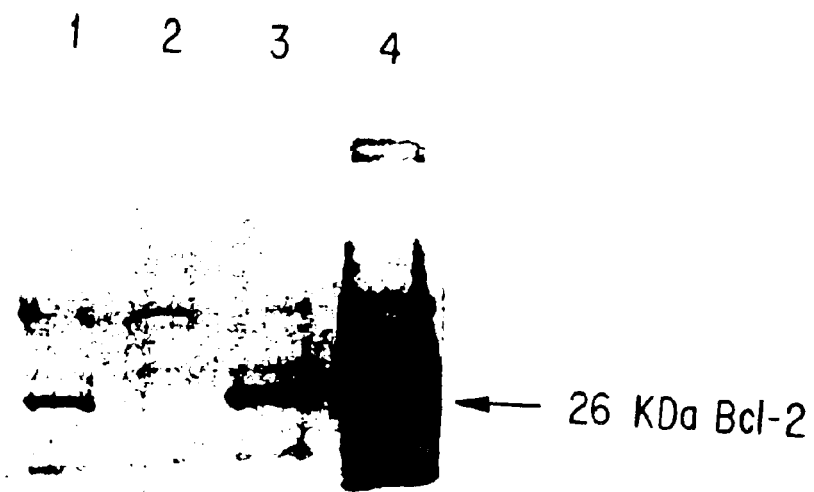
FIG. 3: Western blot analysis of Bcl-2 protein in the four cell lines. Johnson, Jurkat, Daudi and Raji cells were lysed in sample buffer and normalized for total protein content. Twenty-five grams of total protein was loaded in each lane. The membranes were incubated with hamster anti-human bcl-2 monoclonal antibody. In Johnson cells, a cell line bearing the t(14;18) translocation, overexpression of Bcl-2 protein is observed. In Jurkat and Raji cells, which lack the t(14;18) translocation, expression of Bcl-2 is low. In Daudi cells, Bcl-2 expression is not observed.

In order to determine whether the cytotoxic effect of L-bcl-2 in Johnson cells was caused by a decrease in Bcl-2 protein, the Bcl-2 protein expression in these cells after treatment with L-bcl-2 as well as the effects of L-bcl-2 in the other cell lines which overexpress Bcl-2 protein (FIG. 3). was also determined.

When Johnson cells were treated with 2, 3 and 4 μmol/L of L-bcl-2, the ratios of Bcl-2/Actin protein were inhibited by 28, 57 and 64%, respectively. Bcl-2 protein expression was not inhibited in cells treated with the same doses of L-control oligos.

When Jurkat cells were treated with 3 and 4 μmol/L of L-bcl-2, the ratios of Bcl-2/Actin protein were inhibited by 44% and 50%, respectively. Bcl-2 protein was not significantly inhibited when the same doses of L-control oligos were used (FIG. 4).

Figure 5:
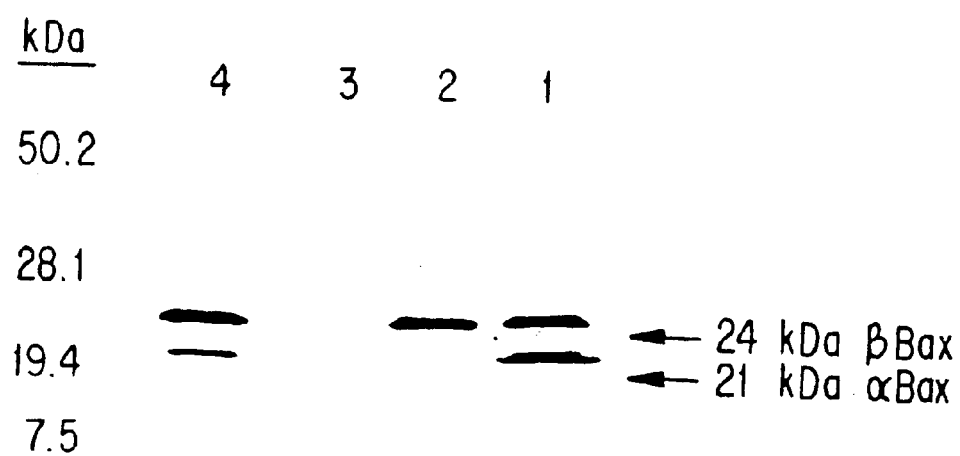
FIG. 5: Western blot analysis of Bax protein in the four cell lines. Johnson, Jurkat, Daudi and Raji cells were lysed in sample buffer and normalized for total protein content. Fifty µg of total protein was loaded in each lane. The membranes were incubated with rabbit anti-human Bax polyclonal antibody.
Figure 4A:
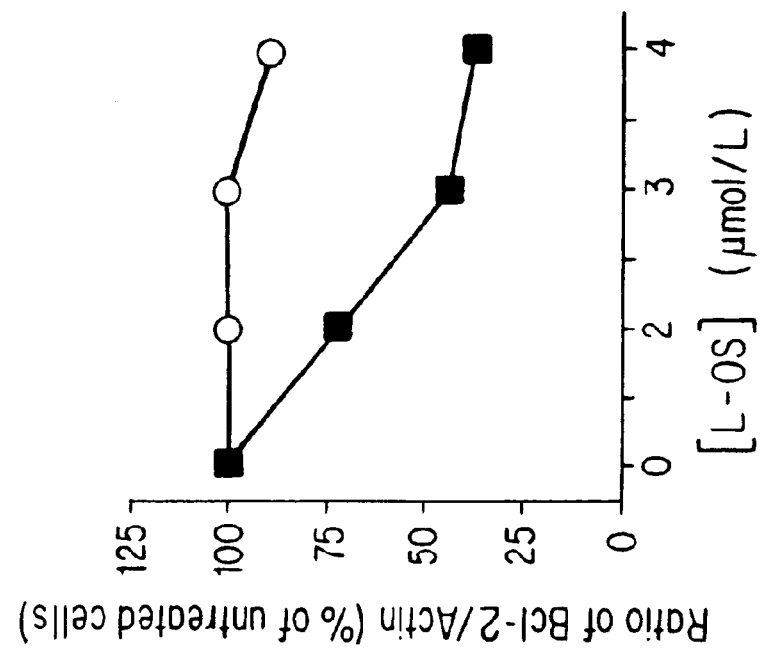
FIG. 4A & FIG. 4B: Specific inhibition of Bcl-2 protein in Johnson and Jurkat cells by L-bcl-2
Figure 4A:
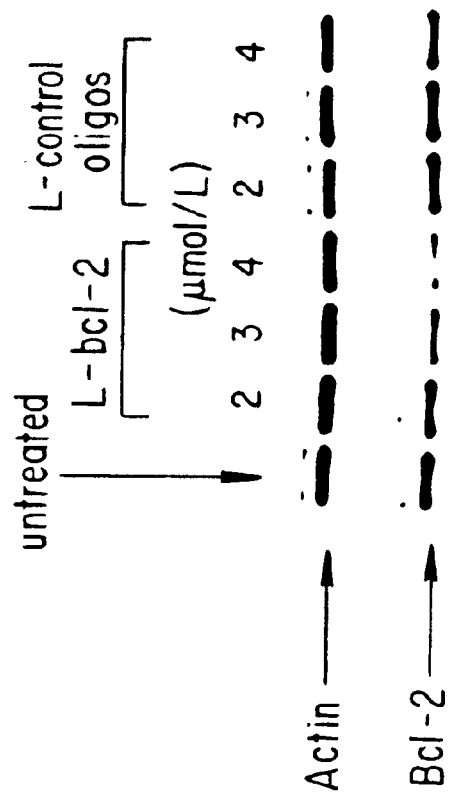
Figure 4B:
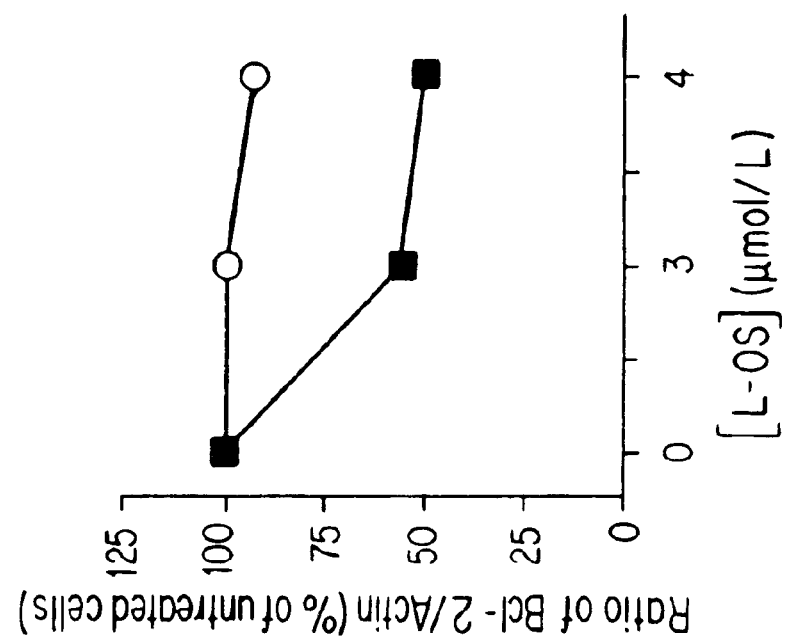
Figure 4B:
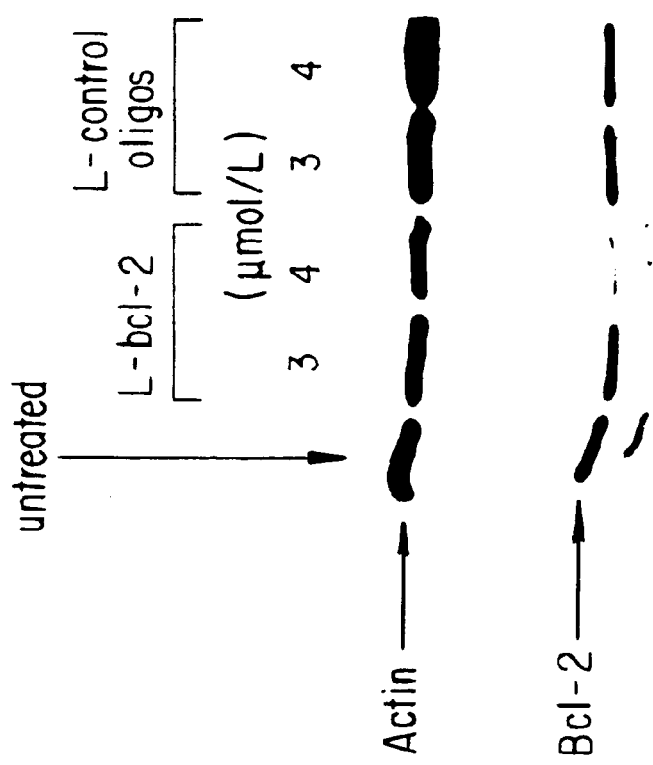
Figure 6A:
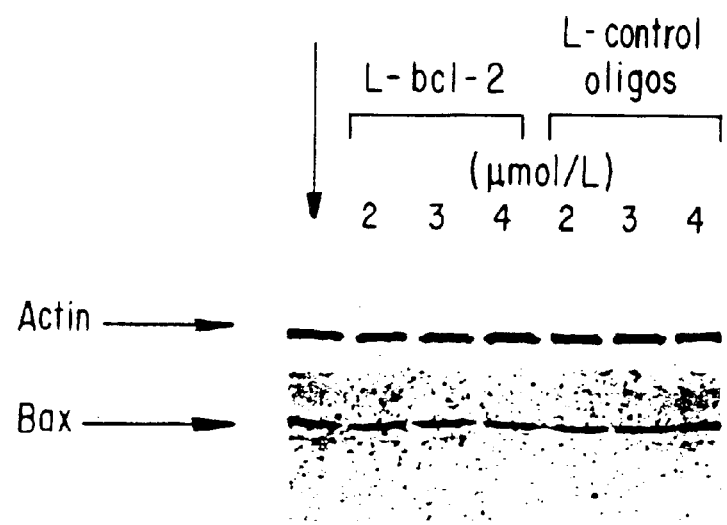
FIG. 6A & FIG. 6B: Bcl-2/Bax ratio decreases in Johnson cells by L-bcl-2.
Figure 6B:
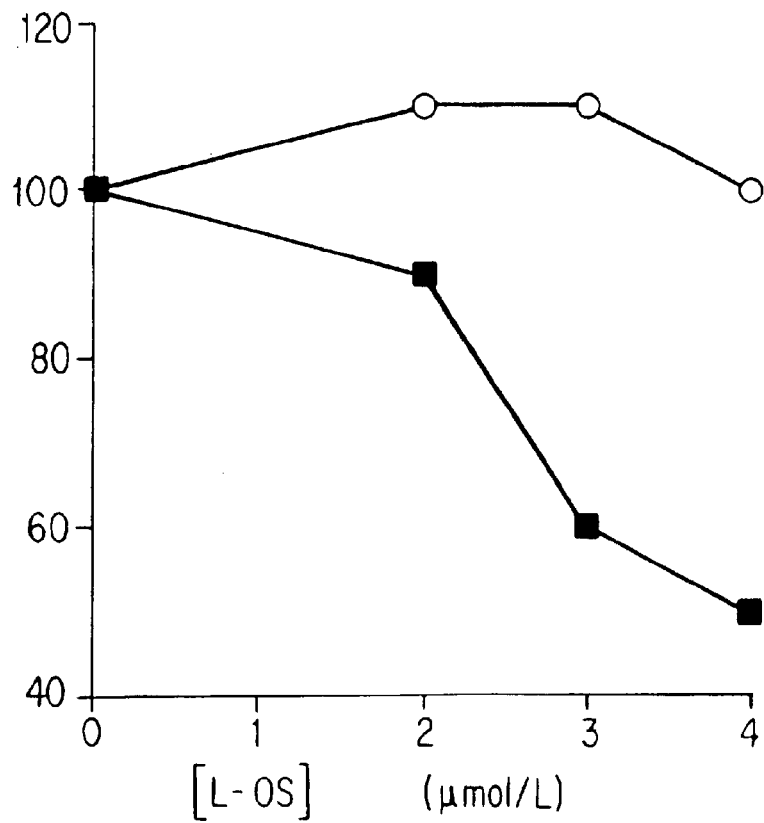

The ratios of Bcl-2/Bax protein in Johnson and Jurkat cells before and after treatment with L-bcl-2 and L-control oligos were also determined. Johnson, Raji and Daudi cells expressed Bax protein but Jurkat cells did not express (FIG. 5). When Johnson cells were treated with 2, 3 and 4 μmol/L of L-bcl-2, the ratio of Bax/Actin was not modified, but the ratio of Bcl-2/Bax decreased by 10%, 40% and 50%, respectively. These protein ratios were unmodified after treatment with the same doses of L-control oligos (FIG. 6).

Inhibition of Bcl-2 Protein Leads to Apoptosis in the FL Cells

Figure 7:
FIG. 7: DNA fragmentation in Johnson cells incubated with L-Bcl-2. Johnson cells were incubated with 4 µmol/L of L-bcl-2 and two L-control oligos. After 3 days of incubation, DNA was extracted, electrophoresed through a 2% agarose gel and stained with ethidium bromide . Lanes1, untreated cells; lane 2, cells treated with L-control (scrambled) oligo; lane 3, cells treated with L-control (random) oligo; lane 4, cells treated with L-bcl-2.
Figure 8A:
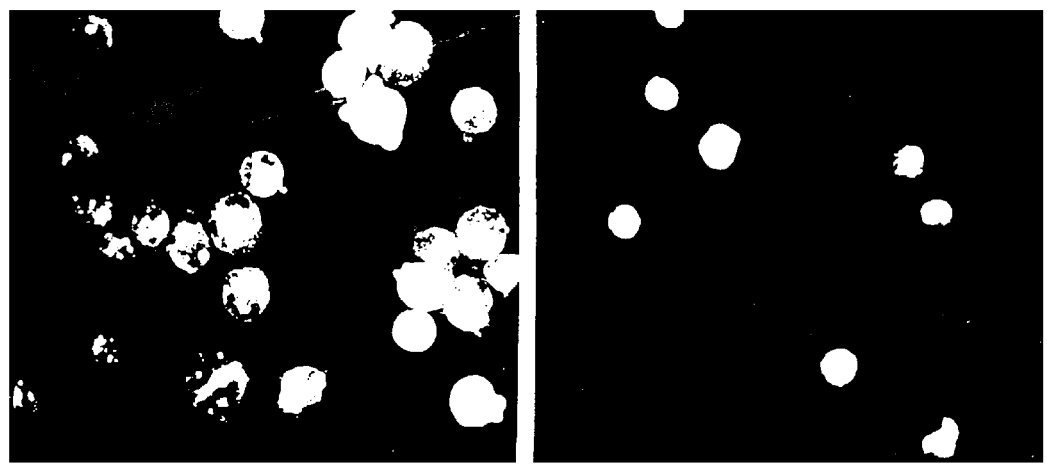
FIG. 8A & FIG. 8B: Apoptotic Johnson cells incubated with L-bcl-2.
Figure 8B:
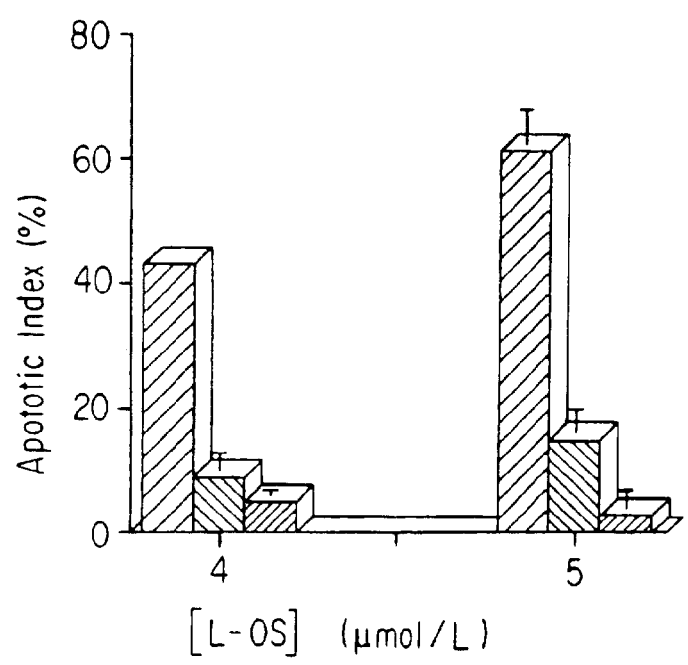

Whether the growth inhibitory effects seen in Johnson cells may be related to induction of apoptosis was also studied. After 3 days of incubation with L-bcl-2, the typical internucleosomal DNA degradation pattern was observed, whereas cells incubated with L-control oligos did not show the internucleosomal DNA pattern (FIG. 7). Subsequently, the quantity of apoptosis by acridine orange was assessed. After 3 days of exposure to 4 and 5 μmol/L of L-bcl-2, apoptotic cells were evident. The apoptotic index of untreated Johnson cells was 3% while that of Johnson cells treated with 4 and 5 μmol/L of L-bcl-2 were 43% and 61%, respectively. Significant increase in apoptotic index was not seen in cells treated with liposomal control oligonucleotides or empty liposomes (FIG. 8).

L-bcl-2 Selectively Downregulates the Expression of Bcl-2 Protein and Cell Growth in a Dose-Dependent Manner The inhibition in cell growth was seen only in the FL cell line which bears the t(14;18) translocation, while cell growth inhibition was not seen in cell lines that lack the Bcl-2 expression (Daudi cells) or the t(14;18) translocation (Raji and Jurkat cells). There was no non-specific toxicity in Johnson cells exposed to two different control oligonucleotides. The growth inhibitory effects could be observed starting at a concentration of 3 μmol/L of L-bcl-2, and the inhibitory effects were maximal at 6 μmol/L concentration. One of the mechanisms by which L-bcl-2 exerts growth inhibition in Johnson cells might be through induction of apoptosis, since treated cells showed a typical DNA internucleosomal degradation pattern, and an increased apoptotic index as measured by acridine orange. By day 3, 61% of Johnson cells treated with 5 μmol/L of L-bcl-2 were in apoptosis as compared with 15% of cells treated with L-control oligos. Apoptosis was not observed in the other cell types.

Thus, the inhibition of Bcl-2 protein leads to cell growth inhibition in cells that are dependent on the presence of Bcl-2 protein for maintaining viability. Gene transfer experiments have provided evidence that Bcl-2 plays an important role in maintaining lymphoid cell survival in vitro, although other autocrine growth factors may also be involved (Vaux et. al, 1988; Reed et. al, 1990b; Blagosklonny and Neckers, 1995). Using phosphorothioate antisense oligonucleotides, Cotter and co-workers observed growth inhibition in DoHH2 cell line which has the t(14;18) translocation and overexpress Bcl-2 protein, but not in FC11 cell line which overexpresses Bcl-2 protein without the t(14;18) translocation (Cotter et. al, 1994). Cells that overexpress Bcl-2 and lack the t(14;18) translocation may need an apoptotic stimulus, like growth factor deprivation or treatment with chemotherapeutic drugs, to be driven into apoptosis and growth arrest (Reed, 1995). Antisense oligonucleotides may be used to reverse the chemotherapeutic resistance of those cells that also overexpress high levels of Bcl-2 without the t(14;18) translocation (Kitada et. al, 1994).

Bax, a promoter of apoptotic cell death, may be a common partner involved in heterodimerization and regulation of other Bcl-2 family members function (Sedlak et. al, 1995). It has been suggested that, the equilibrium in the formation of Bcl-2:Bax heterodimers and Bax:Bax homodimers appears to be central in the molecular regulation of apoptosis (Yin et. al, 1994). Moreover, in a recent study, the ratio of Bcl-2:Bax correlated with cell death in IL-3-dependent FL5.12 cells. When approximately half or more of Bax was heterodimerized with Bcl-2, apoptosis was inhibited (Yang et. al, 1995). The apoptotic death observed in Johnson cells, after incubation with L-bcl-2, could be due to decrease in Bcl-2:Bax ratio and formation of more Bax:Bax homodimers.

Another explanation is that other oncogenes and tumor suppressor genes such as C-MYC and p53 may be involved in the survival of the other cell lines. C-MYC, for example, is typically expressed in Burkitt lymphomas and in some transformed FL (McDonnell and Korsmeyer, 1991). Mutations of p53 gene, a suppressor gene involved in numerous human tumors, may also be involved in these cell lines; p53 gene encodes a DNA-binding protein that functions at least in part as a transcription factor to induce cell cycle arrest and apoptosis by upregulation of Bax (Vogelstein and Kinzler, 1992; Miyashita et. al, 1994; Miyashita and Reed, 1995). Probably, inhibition of Bcl-2 expression alone is not enough to induce apoptosis and growth inhibition in cells other than Johnson cells.

A decrease in the ratio of Bcl-2/Bax by L-bcl-2 forms the basis for a molecular approach to follicular lymphoma therapy.

EXAMPLE 4

In Vivo Testing

In an initial round of in vivo trials, inventors can use a mice model of human cancer with the histologic features and metastatic potential resembling tumors seen in humans and treat these animals with lipid-associated oligo- or polynucleotide compositions to examine the suppression of tumor development.

These studies are based on the discovery that bcl-2 antisense oligonucleotides associated with lipids inhibit the production of the Bcl-2 protein and the growth of t(14;18) translocation bearing cells (Examples 1–3). The Examples above further show that these lipid formulations inhibit the growth of bcl-2-related cancer cells. The current example uses lipid-associated poly- and oligonucleotide formulations, either alone or in combination with chemotherapeutic drugs, to provide a useful preventive and therapeutic regimen for patients with bcl-2-overexpressing cancers.

Mice of a suitable cancer model (see, e.g., McDonnell, 1993) will be treated with doses of lipid-associated oligo- or polynucleotide compositions starting at 8–10 weeks of age or approximately 25 g in weight. The mice used may be transgenic mice bearing the t(14;18) translocation, or they may be nude or SCID mice that were implanted intraperitoneally with human FL cell lines. Several combinations and concentrations of these formulations will be tested. Three groups of mice will be used: untreated mice (or mice injected with buffer only), mice injected with liposomal antisense oligos, and mice injected with liposomal control oligos. The animals will be injected intravenously with liposomal oligos twice a week. The doses will range between 0–15 mg of liposomal oligos per kg of mouse in weight. The treatments will be from 6 to 8 weeks.

The effect of the lipid-associated oligonucleotide compositions on the development of FL tumors will be compared with the control group by measuring tumor size, mouse survival, B cell hyperplasia, and Bcl-2 expression. It is predicted that, unlike the control groups of mice that will develop tumors, the testing group of mice will have decreased Bcl-2 expression, B cell hyperplasia, and tumor size, as well as prolonged survival. The group treated with liposomal control oligos should have no such effects.

EXAMPLE 5

Clinical Trials

This example is concerned with the development of human treatment protocols using the lipid-associated oligo- and polynucleotide compositions. These lipid formulations will be of use in the clinical treatment of various bcl-2-overexpressing cancers and diseases in which transformed or cancerous cells play a role. Such treatment will be particularly useful tools in anti-tumor therapy, for example, in treating patients with FL. This treatment will also be useful in treating other conditions that are mediated by bcl-2 over-expression and resistant to conventional regimens and treatments such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

The various elements of conducting a clinical trial, including patient treatment and monitoring, will be known to those of skill in the art in light of the present disclosure.

The following information is being presented as a general guideline for use in establishing lipid-associated oligo- and polynucleotide compositions alone or in combinations with anti-cancer drugs in clinical trials.

Candidates for the phase 1 clinical trial will be patients on which all conventional therapies have failed. Liposomal Bcl-2 antisense oligos will be administered to them intravenously on a tentative weekly basis. To monitor disease course and evaluate the anti-tumor responses, it is contemplated that the patients should be examined for appropriate tumor markers every month. To assess the effectiveness of the drug, the following parameters will be monitored: tumor size and bone marrow infiltration of the cancer cells. Tests that will be used to monitor the progress of the patients and the effectiveness of the treatments include: physical exam, X-ray, blood work and other clinical laboratory methodologies. In addition, peripheral blood and bone marrow samples will be drawn to assess the modification of the target protein expression. The doses given in the phase 1 study will be escalated as is done in standard phase 1 clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

EXAMPLE 6

Human Treatment and Clinical Protocols

This example describes a protocol to facilitate the treatment of bcl-2-mediated diseases using lipid-associated oligo- or polynucleotide compositions alone or in combination with anti-cancer drugs.

Typically, patients that are candidates for treatment are those with FL although patients with hematologic malignancies, both leukemias and lymphomas; solid tumors like those associated with breast, prostate and colon cancer; and immune disorders may also be treated with the methods of this invention. The typical course of treatment will vary depending upon the individual patient and disease being treated in ways known to those of skill in the art. For example, a patient with FL might be treated in eight week cycles, although longer duration may be used if no adverse effects are observed with the patient, and shorter terms of treatment may result if the patient does not tolerate the treatment as hoped. Each cycle will consist of between 20 and 35 individual doses spaced equally, although this too may be varied depending on the clinical situation.

A patient presenting a bcl-2-mediated condition, like FL, may be treated using the following protocol. Patients may, but need not, have received previous chemo-, radio- or gene therapeutic treatments. Optimally the patient will exhibit adequate bone marrow function (defined as peripheral absolute granulocyte count of >2,000/mm$^3$ and platelet count of 100,000/mm$^3$, adequate liver function (bilirubin 1.5 mg/dl) and adequate renal function (creatinine 1.5 mg/dl).

The over-expression of bcl-2 is typically monitored before, during, and after the therapy. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The lipid-associated oligo- or polynucleotide compositions may be delivered to the patient before, after or concurrently with the other anti-cancer agents.

A typical treatment course may comprise about six doses delivered over a 7 to 21 day period. Upon election by the clinician the regimen may be continued with six doses every three weeks or on a less frequent (monthly, bimonthly, quarterly etc.) basis. Of course, these are only exemplary times for treatment, and the skilled practitioner will readily recognize that many other time-courses are possible.

To kill bcl-2-overexpressing cancer cells using the methods and compositions described in the present invention one will generally contact a target cell with the lipid-associated formulations described previously. These compositions will be provided in an amount effective to kill or inhibit the proliferation of the cell.

Regional delivery of the lipid-associated formulations will be an efficient method for delivering a therapeutically effective dose to counteract the clinical disease. Alternatively systemic delivery may be appropriate. The therapeutic composition of the present invention may be administered to the patient directly at the site of the tumor. This is in essence a topical treatment of the surface of the cancer. The volume of the composition should usually be sufficient to ensure that the entire surface of the tumor is contacted by the lipid-associated oligo- or poly-nucleotide composition.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

Of course, the above-described treatment regimes may be altered in accordance with the knowledge gained from clinical trials such as those described in Example 5. Those of skill in the art will be able to take the information disclosed in this specification and optimize treatment regimes based on the clinical trials described in the specification.

H. References

The following references, to the extent that they provide exemplary procedural or other details supplementary to those set forth herein, are specifically incorporated herein by reference:

Aisenberg, "Coherent view of non-Hodgkin's lymphoma," *J Clin. Oncol.*, 13:2656, 1995.

Akhtar et. al, "Interactions of antisense DNA oligonucleotide analogs with phospholipids membranes (liposomes)," *Nucleic Acids Res.*, 19:5551, 1991.

Baichwal and Sugden, "Vectors for gene transfer derived from animal DNA viruses: Transient and stable expression of transferred genes," In: Kucherlapati R, (ed.) Gene transfer. New York: Plenum Press, pp. 117–148, 1986.

Bakhshi et. al, "Cloning the chromosomal breakpoint of t(14;18) human lymphomas: clustering around JH on chromosome 14 and near a transcriptional unit on 18," *Cell*, 41:899, 1985.

Bangham et al., *J. Mol. Biol.*, 13:238, 1965.

Benvenisty and Neshif, "Direction introduction of genes into rats and expression of the genes," *Proc. Nat'l Acad. Sci. USA*, 83:9551, 1986.

Blagosklonny and Neckers, "The role of Bcl-2 protein and autocrine growth factors in a human follicular lymphoma-derived B cell line," *Eur. Cytokine Network*, 6:21, 1995.

Boise et. al, "BCL-X, a BCL-2-related gene that functions as a dominant regulator of apoptotic cell death," *Cell*, 74:597, 1993.

Campos et al., "Effects of BCL-2 Antisense Oligodeoxynucleotides on In Vitro Proliferation and Survival of Normal Marrow Progenitors and Leukemic Cells," *Blood*, 84:595, 1994.

Chang et al., "Foreign gene delivery and expression in hepatocytes using a hepatitis B virus vector," *Hepatology*, 14:134A, 1991.

Chen and Okayama, "High-efficiency transfection of mammalian cells by plasmid DNA," *Mol. Cell Biol.*, 7:2745–2752, 1987.

Chittenden et. al, "Induction of apoptosis by the Bcl-2 homologue Bak," *Nature*, 374:733, 1995.

Coffin, "Retroviridae and their replication," In: *Virology*, Fields et al. (eds.), New York: Raven Press, pp. 1437–1500, 1990.

Cotter et. al, "Antisense oligonucleotides suppress B-cell lymphoma growth in a SCID-hu mouse model," *Oncogene*, 9:3049, 1994.

Coupar et al., "A general method for the construction of recombinant vaccinia virus expressing multiple foreign genes," *Gene*, 68:1–10, 1988.

Deamer and Uster, "Liposome Preparation: Methods and Mechanisms," *LIPOSOMES*, M. Ostro ed. (1983).

Dubensky et al., "Direct transfection of viral and plasmid DNA into the liver or spleen of mice," *Proc, Nat'l Acad. Sci. USA*, 81:7529–7533, 1984.

Duke et. al, "Morphological, biochemical and flow cytometric assays of apoptosis," In: Coligan et. al (eds) Current protocols in immunology, vol 1., New York: John Wiley & sons, p 3.17.1, 1991.

Fecheimer et. al, "Transfection of mammalian cells with plasmid DNA by scrape loading and sonication loading," *Proc. Nat'l Acad. Sci USA*, 76:3348–52, 1979.

Fraley et al., "Entrapment of a bacterial plasmid in phospholipid vesicles: Potential for gene transfer," *Proc. Nat'l Acad. Sci. USA*, 76:3348–3352, 1979.

Friedman et al., "CCAAT/enhancer-binding protein activates the promoter of the serum albumin gene in cultured hepatoma cells," *Genes Devel.* 3:1314, 1989.

Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87–104, 1991.

Gopal, "Gene transfer method for transient gene expression, stable transfection, and cotransfection of suspension cell cultures," *Mol. Cell Biol.*, 5:1188–1190, 1985.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5 DNA", *J. Gen. Virol.*, 36:59–72, 1977.

Graninger et. al, "Expression of bcl-2 and bcl-2-Ig fusion transcripts in normal and neoplastic cells, " *J. Clin. Invest.*, 80:1512, 1987.

Gregoriadis, *DRUG CARRIERS IN BIOLOGY AND MEDICINE*, G. Gregoriadis (ed.), 1979.

Grunhaus & Horwitz, "Adenovirus as cloning vector," *Seminar in Virology*, 3:237–252, 1992.

Harland and Weintraub, "Translation of mammalian mRNA injected into Xenopus oocytes is specifically inhibited by antisense RNA," *J. Cell Biol.*, 101:1094–1099, 1985.

Hermonat and Muzycska, "Use of adenoassociated virus as a mammalian DNA cloning vector: Transduction of neomycin resistance into mammalian tissue culture cells," *Proc. Nat'l Acad. Sci. USA*, 81:6466–6470, 1984.

Hockenbery et. al, "Bcl-2 is an inner mitochondrial membrane protein that blocks programmed cell death," *Nature*, 348:334, 1990.

Horwich et al., "Synthesis of hepadenovirus particles that contain replication-defective duck hepatitis B virus genomes in cultured HuH7 cells," *J. Virol.* 64:642–650, 1990.

Johnson et. al, "Patterns of survival in patients with recurrent follicular lymphoma: A 20-year study from a single center," *J. Clin. Oncol.*, 13:140, 1995.

Kaneda et al., "Increased expression of DNA cointroduced with nuclear protein in adult rat liver," *Science*, 243:375–378, 1989.

Kato et al., "Expression of hepatitis B virus surface antigen in adult rat liver," *J. Biol. Chem.*, 266:3361–3364, 1991.

Kiefer et. al, "Modulation of apoptosis by the widely distributed Bcl-2 homologue Bak," *Nature*, 374: 736, 1995.

Kitada et al., "Reversal of chemoresistance of lymphoma cells by antisense-mediated reduction of bcl-2 gene expression," *Antisense Res. Dev.*, 4:71, 1994.

Kitada et. al, "Investigations of antisense oligonucleotides targeted against bcl-2 RNAs," *Antisense Res. Dev.*, 3:157, 1993.

Klein et al., "High-velocity microprojectiles for delivering nucleic acids into living cells," *Nature*, 327:70–73, 1987.

Kozopas et. al "MCL-1, a gene expressed in programmed myeloid cell differentiation, has sequence similarity to BCL-2," *Proc. Nat'l Acad. Sci. USA*, 90:3516, 1993.

Lin et. al, "Characterization of A1, a novel hemopoietic-specific early-response gene with sequence similarity to BCL-2," *J. Immunol.*, 151:1979, 1993.

Mann et al., "Construction of a retrovirus packaging mutant and its uses to produce helper-free defective retrovirus," *Cell*, 33:153–159, 1983.

McDonnell, "The bcl-2-Immunoglobulin Transgenic Mouse: A Model of the t(14;18) Translocation in Human Follicular Lymphoma," *Transgene*, 1:47, 1993.

McDonnell and Korsmeyer, "Progression from lymphoid hyperplasia to high-grade malignant lymphoma in mice transgenic for the t(14;18)," *Nature*, 349:254, 1991.

McDonnell et. al, "Bcl-2-immunoglobulin transgenic mice demonstrate extended B cell survival and follicular lymphoproliferation," *Cell*, 57:79, 1989.

Miyashita et. al, "Tumor suppressor p53 is a regulator of bcl-2 and bax gene expression in vitro and in vivo," *Oncogene*, 9:1799, 1994.

Miyashita and Reed, "Tumor suppressor p53 is a direct transcriptional activator of the human BAX gene," *Cell*, 80:293, 1995.

Neilan et. al, "An African Swine fever virus with similarity to the protooncogene BCL-2 and the Epstein-Barr virus gene BHRF1, " *J. Virol.*, 67:4391, 1993.

Nicolas and Rubenstein, "Retroviral vectors," In: *Vectors: A survey of molecular cloning vectors and their uses*, Rodriguez and Denhardt, (eds.), Stoneham: Butterworth, pp. 494–513, 1988.

Nicolau et al., "Liposomes as carriers for in vivo gene transfer and expression," *Methods Enzymol.*, 149:157–176, 1987.

Nicolau and Sene, "Liposome-mediated DNA transfer in eukaryotic cells," *Biochem. Biophys. Acta*, 721:185–190, 1982.

Nuñez et. al, "Deregulated BCL-2 gene expression selectively prolongs survival of growth factors-deprived hemopoietic cell lines," *J. Immunol.*, 144:3602, 1990.

Oltvai et. al, "Bcl-2 heterodimerizes in vivo with a conserved homolog, bax, that accelerates programmed cell death," *Cell*, 74:609, 1993.

Paskind et al., "Dependence of moloney murine leukemia virus production on cell growth," *Virology*, 67:242–248, 1975.

Pearson et. al, "Identification of an Epstein-Barr virus early gene encoding a second component of the restricted early antigen complex," *Virology*, 160:151, 1987.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Reed, "Bcl-2: prevention of apoptosis as a mechanism of drug resistance, " *Hematol. Oncol. Clin. North Am.*, 9:451, 1995.

Reed et. al, "Antisense-mediated inhibition of bcl-2 protooncogene expression and leukemic cell growth and survival: comparisons of phosphodiester and phosphorothioate oligodeoxynucleotides," *Cancer Research*, 50: 6565, 1990a.

Reed et al., "Bcl-2-mediated tumorigenicity in a human T-lymphoid cell line: synergy with c-myc and inhibition by Bcl-2 antisense," *Proc. Nat'l Acad. Sci. USA*, 87:3660, 1990b.

Ridgeway, "Mammalian expression vectors," In: Rodriguez R L, Denhardt D T, (ed.) Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Sato et. al, "Investigations of bcl-2 protein family interactions using yeast two-hybrid system," *Proc. Nat'l Acad. Sci. USA*, 91:9238, 1994.

Sedlak et. al, "Multiple bcl-2 family members demonstrate selective dimerization with bax," *Proc. Nat'l Acad. Sci. USA*, 92:7834, 1995.

Stratford-Perricaudet and Perricaudet, "Gene transfer into animals: the promise of adenovirus," pp. 51–61, *In: Human Gene Transfer*, Eds, O. Cohen-Haguenauer and M. Boiron Editions John Libbey Exrotext, France, 1991.

Szoka and Papahadjopoulos, *Proc. Nat'l Acad. Sci. U.S.A*. 75:4194–98 (1978).

Tari et. al, "Liposomal delivery of methylphosphonate antisense oligodeoxynucleotides in chronic myelogenous leukemia," *Blood*, 84:601, 1994.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149–188, 1986.

Tsujimoto et. al, "Characterization of the protein product of bcl-2, the gene involved in human follicular lymphoma," *Oncogene*, 2:3, 1987.

Tsujimoto and Croce, "Analysis of the Structure, Transcripts, and Protein Products of bcl-2, the gene involved in Human Follicular," *Proc. Natl. Acad. Sci. USA*, 83:5214, 1986.

Tsujimoto et. al, "The t(14;18) chromosome translocation involved in B-cell neoplasms result from mistakes in VDJ joining," *Science*, 229:1390, 1985.

Tur-Kaspa et al., "Use of electroporation to introduce biologically active foreign genes into primary rat hepatocytes," *Mol. Cell Biol.*, 6:716–718, 1986.

Vaux et. al, "Bcl-2 promotes hemapoietic cell survival and cooperates with c-myc to immortalize pre-B cells," *Nature* (London), 355: 440, 1988.

Vogelstein and Kinzler, "p53 function and dysfunction," *Cell*, 70:523, 1992.

Wagner et al., *Science*, 260:1510–1513, 1993.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Yang et. al, "Bad, a heterodimeric partner for Bcl-$X_L$ and Bcl-2, displaces Bax and promotes cell death," *Cell*, 80:285, 1995.

Yang et al., "In vitro and in vivo gene transfer to mammalian somatic cells by particle bombardment," *Proc. Nat'l Acad. Sci. USA*, 87:9568–9572, 1990.

Yin et. al, "BH1 and BH2 domains of Bcl-2 are required for inhibition of apoptosis and heterodimerization with Bax," *Nature*, 369: 321, 1994.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

---

What is claimed is:

1. A method of inhibiting proliferation of a Bcl-2-associated disease cell comprising obtaining a polynucleotide that hybridizes to Bcl-2 mRNA under intracellular conditions, mixing the first polynucleotide with a neutral phospholipid to form a composition comprising a polynucleotide/phospholipid association, and administering said composition to a human having a Bcl-2-associated disease to inhibit the proliferation of said disease cells, wherein said disease cells have a t(14;18) translocation, wherein said composition is delivered to said human in an amount of from about 5 to about 30 mg polynucleotide per m².

2. The method of claim 1, wherein the cell is a cancer cell.

3. The method of claim 2, wherein said cancer cell is a follicular lymphoma cell.

4. The method of claim 1, wherein said first polynucleotide is an oligonucleotide having a length of between about 8 and about 50 bases.

5. The method of claim 1, comprising a liposome formed from the phospholipid.

6. The method of claim 5, wherein the liposome encapsulates the first polynucleotide.

7. The method of claim 1, wherein said composition is delivered to said human in a volume of 0.50–10.0 ml per dose.

8. The method of claim 1, wherein said composition is administered three times per week for eight weeks.

9. A method of inhibiting proliferation of a Bcl-2-associated disease cell having a t(14;18) translocation comprising:

(a) obtaining an oligonucleotide of from about 8 to about 50 bases that hybridizes to a Bcl-2-encoding polynucleotide under intracellular condition;

(b) mixing the oligonucleotide with a neutral phospholipid to form a composition comprising a neutral oligonucleotide/phospholipid association; and (c) administering said composition to said Bcl-2-associated disease cell to inhibit the proliferation of said disease cell, wherein said cell is in a human, and wherein said composition is delivered to said human in an amount of from about 5 to about 30 mg polynucleotide per m².

10. The method of claim 9, wherein the cell is a cancer cell.

11. The method of claim 10, wherein said cancer cell is a follicular lymphoma cell.

12. The method of claim 9, comprising a liposome formed from the phospholipid.

13. The method of claim 12, wherein the liposome encapsulates the polynucleotide.

14. The method of claim 9, wherein said composition is delivered to said human in a volume of 0.50–10.0 ml per dose.

15. The method of claim 9, wherein said composition is administered three times per week for eight weeks.

16. The method of claim 5, wherein said liposome consists essentially of neutral phospholipids.

17. The method of claim 12, wherein said liposome consists essentially of neutral phospholipids.

18. A composition comprising a first antisense polynucleotide that hybridizes to a second, Bcl-2-encoding polynucleotide under intracellular conditions and a neutral phospholipid associated with said first polynucleotide, to form a Bcl-2 polynucleotide/neutral phospholipid association, wherein said first polynucleotide comprises at least 8 nucleotides of the sequence CAGCGTGCGCCATCCTTC (SEQ ID NO:1), wherein said polynucleotide is complementary to the translation initiation site of Bcl-2, said composition further comprising a charged phospholipid.

19. The composition of claim 18, wherein said first polynucleotide is an oligonucleotide having a length of between about 8 and about 50 bases.

20. The composition of claim 18, wherein the first polynucleotide is complementary to the translation initiation site of Bcl-2 mRNA.

21. The composition of claim 20, wherein the polynucleotide is an oligonucleotide comprising the sequence CAGCGTGCGCCATCCTTC (SEQ ID NO:1).

22. The composition of claim 18, comprising a liposome formed from the phospholipid.

23. The composition of claim 22, wherein the first polynucleotide is encapsulated in the liposome.

24. The composition of claim 18, wherein the phospholipid is a phosphatidylcholine, a phosphatidylglycerol, or a phosphatidylethanolamine.

25. The composition of claim 24, wherein the phospholipid is dioleoylphosphatidylcholine.

26. A composition comprising an expression construct that encodes a first antisense polynucleotide that hybridizes to a second, Bcl-2-encoding polynucleotide under intracellular conditions, wherein said construct is under the control of a promoter that is active in eukaryotic cells and associated with a neutral phospholipid, wherein said first polynucleotide comprises at least 8 nucleotides of the sequence CAGCGTGCGCCATCCTTC (SEQ ID NO:1), wherein said polynucleotide is complementary to the translation initiation site of Bcl-2, further comprising a charged phospholipid.

27. A composition comprising a neutral phospholipid associated with an expression construct that encodes an oligonucleotide of from about 8 to about 50 bases and which hybridizes to Bcl-2 mRNA under intracellular conditions, wherein the construct is under the control of a promoter that is active in eukaryotic cells, further comprising a charged phospholipid.

28. The composition of claim 18, wherein said first polynucleotide is a P-ethoxy oligonucleotide.

29. The composition of claim 22, wherein said liposome consists essentially of neutral and charged phospholipids.

30. The composition of claim 26, comprising a liposome formed from said neutral phospholipid.

31. The composition of claim 30, wherein said liposome consists essentially of neutral and charged phospholipids.

32. The composition of claim 27, comprising a liposome formed from the phospholipid.

33. The composition of claim 32, wherein said liposome consists essentially of neutral and charged phospholipids.

34. A composition comprising a first antisense polynucleotide that hybridizes to a second, Bcl-2-encoding polynucleotide under intracellular conditions and a primary phosphatide associated with said first polynucleotide, wherein said primary phosphatide is a neutral phospholipid, and wherein said first polynucleotide comprises at least 8 nucleotides of the sequence CAGCGTGCGCCATCCTTC (SEQ ID NO:1), and wherein said polynucleotide is complementary to the translation initiation site of Bcl-2, further comprising a charged phospholipid.

35. The composition of claim 34, comprising a liposome formed from the primary phosphatide.

36. The composition of claim 35, wherein said liposome consists essentially of neutral and charged phospholipids.

37. The composition of claim 34, wherein said first polynucleotide is a P-ethoxy oligonucleotide.

38. The composition of claim 18, wherein said at least 8 nucleotides are consecutive nucleotides.

39. The composition of claim 18, wherein the charged phospholipid is a positively charged phospholipid.

40. A method of inhibiting proliferation of a Bcl-2-associated disease cell comprising obtaining a polynucleotide that hybridizes to Bcl-2 mRNA under intracellular conditions, mixing the first polynucleotide with a neutral phospholipid to form a composition comprising a polynucleotide/phospholipid association, and administering said composition to a human having a Bcl-2-associated disease to inhibit the proliferation of said disease cells, wherein said disease cells have a t(14;18) translocation, the composition further comprising a charged phospholipid.

41. The method of claim 40, wherein the charged phospholipid is a positively charged phospholipid.

42. The method of claim 1, wherein said first polynucleotide is a ethoxy oligonucleotide.

43. The method of claim 9, wherein said first oligonucleotide is a P-ethoxy oligonucleotide.

* * * * *

UNITED STATES PATENT AND TRADEMARK OFFICE
CERTIFICATE OF CORRECTION

PATENT NO. : 6,977,244 B2
DATED : December 20, 2005
INVENTOR(S) : Tormo et al

It is certified that error appears in the above-identified patent and that said Letters Patent is hereby corrected as shown below:

Column 40,
Line 40, delete "condition" and insert -- conditions --.

Column 42,
Line 43, delete "ethoxy" and insert -- P-ethoxy --.

Signed and Sealed this

Twenty-third Day of May, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,977,244 B2 | Page 1 of 1 |
| APPLICATION NO. | : 08/726211 | |
| DATED | : December 20, 2005 | |
| INVENTOR(S) | : Mar Tormo et al. | |

It is certified that error appears in the above-identified patent and that said Letters Patent is hereby corrected as shown below:

In Title Page, Item (63) Related U.S. Application Data, please insert --Continuation of Application No. 08/726,211, filed October 4, 1996, now Patent 6,977,244.--.

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 6,977,244 B2  Page 1 of 1
APPLICATION NO. : 08/726211
DATED : December 20, 2005
INVENTOR(S) : Mar Tormo et al.

It is certified that error appears in the above-identified patent and that said Letters Patent is hereby corrected as shown below:

In Title Page, Item (63) Related U.S. Application Data, please insert --Continuation of Application No. 08/726,211, filed October 4, 1996, now Patent 6,977,244.--.

Signed and Sealed this

Twenty-sixth Day of February, 2008

JON W. DUDAS
*Director of the United States Patent and Trademark Office*